US006090929A

United States Patent [19]
Scott et al.

[11] Patent Number: 6,090,929
[45] Date of Patent: Jul. 18, 2000

[54] PROTEIN BINDING FRAGMENTS OF GRAVIN

[75] Inventors: John D. Scott; J. Brian Nauert; Theresa M. Klauck, all of Portland, Oreg.

[73] Assignee: Oregon Health Science University, Portland, Oreg.

[21] Appl. No.: 08/994,570

[22] Filed: Dec. 19, 1997

Related U.S. Application Data

[63] Continuation-in-part of application No. 08/769,309, Dec. 19, 1996, Pat. No. 5,741,890.

[51] Int. Cl.[7] .......................... C07H 21/04; C12N 15/12; C12N 15/63
[52] U.S. Cl. .................... 536/23.5; 435/69.1; 435/320.1; 435/252.3; 435/254.11; 530/350
[58] Field of Search .................................. 536/23.5, 23.1; 435/69.1, 320.1, 252.3, 254.11; 530/350

[56] References Cited

U.S. PATENT DOCUMENTS

| | | | |
|---|---|---|---|
| 4,766,046 | 8/1988 | Abra et al. | 424/450 |
| 5,169,637 | 12/1992 | Lenk et al. | 424/450 |
| 5,180,713 | 1/1993 | Abra et al. | 514/31 |
| 5,185,154 | 2/1993 | Lasic et al. | 124/450 |
| 5,204,112 | 4/1993 | Hope et al. | 124/450 |
| 5,252,263 | 10/1993 | Hope et al. | 264/4.3 |

FOREIGN PATENT DOCUMENTS

WO 92/02244  2/1992  WIPO .

OTHER PUBLICATIONS

Aderem, A., "The MARCKS Brothers: A Family of Protein Kinase C Substrates," *Cell*, 71:713–716 (1992).
Cappecchi, M., "Altering the Genome by Homologous Recombination," *Science*, 244:1288–1292 (1989).
Carr et al., "Interaction of the Regulatory Subunit (RII) of cAMP–dependent Protein Kinase with RII–anchoring Proteins Occurs Through an Amphipathic Helix Binding Motif," *J. Biol. Chem.*, 266:14188–14192 (1991).
Carr et al., "Association of the Type II cAMP–dependent Protein Kinase with a Human Thyroid RII–anchoring Protein," *J. Biol. Chem.*, 267:13376–13382 (1992).
Chapline et al., "Interaction Cloning of Protein Kinase C Substrates," *J. Biol. Chem.*, 268:6858–6861 (1993).
Chapline et al., "Identification of a Major Protein Kinase C–binding Protein and Substrate in Rat Embryo Fibroblasts," *J. Biol. Chem.*, 271:6417–6422 (1996).
Cheley et al., "Type II Regulatory Subunits of cAMP–dependent Protein Kinase and Their Binding Proteins in the Nervous System of *Aplysia californica*," *J. Biol. Chem.*, 269:2911–2920 (1994).
Chen et al., "Molecular Cloning of cDNA Encoding the 110 kDa and 21 kDa Regulatory Subunits of Smooth Muscle Protein Phosphatase 1M," *FEBS Letters*, 356:51–55 (1994).
Choi et al., "Ste5 Tethers Multiple Protein Kinases in the MAP kinase Cascade Required for Mating in *S. cerevisiae*," *Cell*, 78:499–512 (1994).

Coghlan et al., "Cloning and Characterization of AKAP 95, a Nuclear Protein that Associates with the Regulatory Subunit of Type II cAMP–dependent Protein Kinase," *J. Biol. Chem.*, 269:7658–7665 (1994).
Coghlan et al., "A Targeting Model for Reversible Phosphorylation," *Advances in Protein Phosphatases*, 9:51–61 (1995a).
Coghlan et al., "Association of Protein Kinase A and Protein Phosphatase 2B with a Common Anchoring Protein," *Science*, 267:108–111 (1995b).
Csortos et al., "High Complexity in the Expression of the B' Subunit of Protein Phosphatase $2A_0$," *J. Biol. Chem.*, 271:2578–2588 (1996).
Davies et al., "The Resonant Mirror: A Versatile Tool for the Study of Biomolecular Interactions," *Techniques in Protein Chemistry*, 5:285–292 (1994).
De Camilli et al., Heterogeneous Distribution of the cAMP Receptor Protein RII in the Nervous System: Evidence for its Intracellular Accumulation on Microtubules, Microtubule–organizing Centers, and in the Area of the Golgi Complex, *J. Cell. Biol.*, 103:189–203 (1986).
Eichholtz et al., "A Myristoylated Pseudosubstrate Peptide, a Novel Protein Kinase C Inhibitor," *J. Biol. Chem.*, 268:1982–1986 (1993).
Faux and Scott, "Molecular Glue: Kinase Anchoring and Scaffold Proteins," *Cell*, 85:9–12 (1996a).
Faux and Scott, "More on Target with Protein Phosphorylation: Conferring Specificity by Location," *TIBS*, 21:312–315 (1996b).
Gill, G.N., "The Enigma of LIM Domains," *Structure*, 3:1285–1289 (1995).
Gluck and Ben–Ze'ev, "Modulation of α–actinin Levels Affects Cell Motility and Confers Tumorigenicity on 3T3 Cells," *J. Cell Science*, 107:1773–1782 (1994).
Gordon et al., "Molecular Cloning and Preliminary Characterization of a Novel Cytoplasmic Antigen Recognized by Myasthenia Gravis Sera," *J. Clin. Invest.*, 90:992–999 (1992).
Grove et al., "Restricted Endothelial Cell Expression of Gravin In Vivo," *Anat. Rec.*, 239:231–242 (1994).
Herskowitz, "MAP Kinase Pathways in Yeast: For Mating and More," *Cell*, 80:187–197 (1995).

(List continued on next page.)

*Primary Examiner*—Paula K. Hutzell
*Assistant Examiner*—Nirmal S. Basi
*Attorney, Agent, or Firm*—Marshall, O'Toole, Gerstein, Murray & Borun

[57] ABSTRACT

The present invention generally relates to protein binding fragments of gravin and polynucleotides encoding these fragments. The protein binding fragments include fragments which bind to the Type II regulatory subunit of cAMP-dependent protein kinase or protein kinase C. This invention further provides antibodies to the protein binding fragments and assays for identifying compounds which modulate the binding of gravin to the binding protein.

12 Claims, 2 Drawing Sheets

OTHER PUBLICATIONS

Hibbs et al., "The Cytoplasmic Domain of the Integrin Lymphocyte Function–associated Antigen 1 β Subunit: Sites Required for Binding to Intercellular Adhesion Molecule 1 and the Phorbol Ester–stimulated Phosphorylation Site," *J. Exp. Med.*, 174:1227–1238 (1991).

Hunter, T., "Protein Kinases and Phosphatases: The Yin and Yang of Protein Phosphorylation and Signaling," *Cell*, 80:225–236 (1995).

Klauck et al., "Coordination of Three Signaling Enzymes by AKAP79, a Mammalian Scaffold Protein," *Science*, 271:1589–1592 (1996).

Liao et al., "Protein Kinase C Domains Involved in Interactions with Other Proteins," *Biochem.*, 33:1229–1233 (1994).

Lin et al., "A Novel src– and ras–suppressed Protein Kinase C Substrate Associated with Cytoskeletal Architecture," *J. Biol. Chem.*, 271:28430–28438 (1996).

Lin et al., "Isolation and Characterization of a Novel Mitogenic Regulatory Gene, 322, Which is Transcriptionally Suppressed in Cells Transformed by src and ras," *Mol. Cell. Biol.*, 15:2754–2762 (1995).

Lohman, et al., "High–affinity Binding of the Regulatory Subunit ($R_{II}$) of a cAMP–dependent Protein Kinase to Microtubule–associated and other Cellular Proteins," *Proc. Nat. Acad. Sci.*, 81:6723–6727 (1984).

Mochly–Rosen, D., "Localization of Protein Kinases by Anchoring Proteins: A Theme in Signal Transduction," *Science*, 268:247–251 (1995).

Mochly–Rosen et al., "Identification of Intracellular Receptor Proteins for Activated Protein Kinase C," *Proc. Natl. Acad. Sci. U.S.A.*, 88:3997–4000 (1991).

Newton, A.C., "Seeing Two Domains," *Current Biology*, 5:973–976 (1995).

Newton, A.C., "Protein Kinase C: Ports of Anchor in the Cell," *Current Biology*, 6:806–809 (1996).

Orr et al., "Requirement for Negative Charge on "Activation Loop" of Protein Kinase C," *J. Biol. Chem.*, 269:27715–27718 (1994).

Papayannopoulou et al., "Human Erythroleukemia Cell Line (HEL) Undergoes a Drastic Macrophage–Like Shift with TPA," *Blood*, 62:832–845 (1983).

Rosenmund et al., "Anchoring of Protein Kinase A is Required for Modulation of AMPA/kainate Receptors on Hippocampal Neurons," *Nature*, 368:853–856 (1994).

Rubino et al., "Localization and Characterization of the Binding Site for the Regulatory Subunit of Type II cAMP–Dependent Protein Kinase on MAP2," *Neuron*, 3:631–638 (1989).

Sambrook et al., 9.47–9.51 in Molecular Cloning, Cold Spring Harbor Laboratory Press, Cold Spring Harbor, New York (1989).

Scott and McCartney, "Localization of A–Kinase through Anchoring Proteins," *Molecular Endocrinology*, 8:5–11 (1994).

Scott et al., "The Molecular Cloning of a Type II Regulatory Subunit of the cAMP–dependent Protein Kinase from Rat Skeletal Muscle and Mouse Brain," *Pro. Nat. Acad. Sci. U.S.A.*, 84:5192–5196 (1987).

Shibasaki et al., "Role of Kinases and the Phosphatase Calcineurin in the Nuclear Shuttling of Transcription Factor NF–AT4," *Nature*, 382:370–373 (1996).

Staudinger et al., "PCK1: A Perinuclear Binding Protein and Substrate for Protein Kinase C Isolated by the Yeast Two–hybrid System," *J. Cell. Biol.*, 128:263–271 (1995).

Stewart and Young, *Solid Phase Peptide Synthesis, 2nd Ed.*, Pierce Chemical Company (1984).

Tam et al., "$S_N2$ Deprotection of Synthetic Peptides with a Low Concentration of HF in Dimethyl Sulfide: Evidence and Application in Peptide Synthesis," *J. Am. Chem. Soc.*, 105:6442–6455 (1983).

Theurkauf et al., "Molecular Characterization of the cAMP–dependent Protein Kinase Bound to Microtubule–associated Protein 2," *J. Biol. Chem.*, 257:3284–3290 (1982).

Valmu et al., "Treatment with Okadaic Acid Reveals Strong Threonine Phosphorylation of CD18 after Activation of CD11/CD18 Leukocyte Integrins with Phorbol Esters or CD3 Antibodies," *J. Immunol.*, 155:1175–1183 (1995).

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 57 amino acids
      (B) TYPE: amino acid
      (C) STRANDEDNESS: single
      (D) TOPOLOGY: linear (xi) SEQUENCE DESCRIPTION: SEQ ID NO:1:

```
Val Ala Ile Glu Asp Leu Glu Pro Glu Asn Gly Ile Leu Glu Leu Glu
1               5                   10                  15

Thr Lys Ser Ser Lys Leu Val Gln Asn Ile Ile Gln Thr Ala Val Asp
                20                  25                  30

Gln Phe Val Arg Thr Glu Thr Ala Thr Glu Met Leu Thr Ser Glu
            35                  40                  45

Leu Gln Thr Gln Ala His Val Ile Lys
50                  55
```

(2) INFORMATION FOR SEQ ID NO:2:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO:2:

```
Ile Leu Glu Leu Glu Thr Lys Ser Ser Lys Leu Val Gln Asn Ile Ile
1               5                   10                  15

Gln Thr Ala Val Asp Gln Phe Val Arg Thr Glu
            20                  25
```

(2) INFORMATION FOR SEQ ID NO:3:

(i) SEQUENCE CHARACTERISTICS:
        (A) LENGTH: 292 amino acids
        (B) TYPE: amino acid
        (C) STRANDEDNESS: single
        (D) TOPOLOGY: linear (xi) SEQUENCE DESCRIPTION: SEQ ID NO:3:

```
Lys Glu Glu Gly Glu Glu Lys Gln Glu Lys Glu Pro Ser Lys Ser Ala
1               5                   10                  15

Glu Ser Pro Thr Ser Pro Val Thr Ser Glu Thr Gly Ser Thr Phe Lys
                20                  25                  30

Lys Phe Phe Thr Gln Gly Trp Ala Gly Trp Arg Lys Lys Thr Ser Phe
            35                  40                  45

Arg Lys Pro Lys Glu Asp Glu Val Glu Ala Ser Glu Lys Lys Lys Glu
50                  55                  60

Gln Glu Pro Glu Lys Val Asp Thr Glu Asp Gly Lys Ala Glu Val
65                  70                  75                  80

Ala Ser Glu Lys Leu Thr Ala Ser Glu Gln Ala His Pro Gln Glu Pro
                85                  90                  95

Ala Glu Ser Ala His Glu Pro Arg Leu Ser Ala Glu Tyr Glu Lys Val
            100                 105                 110

Glu Leu Pro Ser Glu Gln Val Ser Gly Ser Gln Gly Pro Ser Glu
            115                 120                 125

Glu Lys Pro Ala Pro Leu Ala Thr Glu Val Phe Asp Glu Lys Ile Glu
    130                 135                 140

Val His Gln Glu Glu Val Val Ala Glu Val His Val Ser Thr Val Glu
145                 150                 155                 160

Glu Arg Thr Glu Glu Gln Lys Thr Glu Val Glu Glu Thr Ala Gly Ser
                165                 170                 175

Val Pro Ala Glu Glu Leu Val Gly Met Asp Ala Glu Pro Gln Glu Ala
            180                 185                 190

Glu Pro Ala Lys Glu Leu Val Lys Leu Lys Glu Thr Cys Val Ser Gly
        195                 200                 205
```

```
Glu Asp Pro Thr Gln Gly Ala Asp Leu Ser Pro Asp Glu Lys Val Leu
    210                 215                 220

Ser Lys Pro Pro Glu Gly Val Val Ser Glu Val Glu Met Leu Ser Ser
225                 230                 235                 240

Gln Glu Arg Met Lys Val Gln Gly Ser Pro Leu Lys Lys Leu Phe Thr
                245                 250                 255

Ser Thr Gly Leu Lys Lys Leu Ser Gly Lys Lys Gln Lys Gly Lys Arg
                260                 265                 270

Gly Gly Gly Asp Glu Glu Ser Gly Glu His Thr Gln Val Pro Ala Asp
            275                 280                 285

Ser Pro Asp Ser
    290

(2) INFORMATION FOR SEQ ID NO:4:

(i) SEQUENCE CHARACTERISTICS:
        (A) LENGTH: 6605 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 192..5531

(xi) SEQUENCE DESCRIPTION: SEQ ID NO:4:

CCTTCTTTTA AGGAGTTTGC CGCGAGCGCG TCTCCTTCAT TCGCAGGCTG GGCGCGTTCG      60

CAGTCGGCTG GCGGCGAAGG AAGGCGCTCT CGGGACCTCA CGGGCGCGCG TCTTTTGGCT     120

CTTGCCCCTG TCCCTGCGGC TTGGGGAAAG CGTAACCCGG CGGCTAGGCG CGGGAGAAGT     180

GCGGAGGAGC C ATG GGC GCC GGG AGC TCC ACC GAG CAG CGC AGC CCG GAG      230
             Met Gly Ala Gly Ser Ser Thr Glu Gln Arg Ser Pro Glu
              1               5                  10

CAG CCG CCC GAG GGG AGC TCC ACG CCG GCT GAG CCC GAG CCC AGC GGC       278
Gln Pro Pro Glu Gly Ser Ser Thr Pro Ala Glu Pro Glu Pro Ser Gly
 15                  20                  25

GGC GGC CCC TCG GCC GAG GCG GCG CCA GAC ACC ACC GCG GAC CCC GCC       326
Gly Gly Pro Ser Ala Glu Ala Ala Pro Asp Thr Thr Ala Asp Pro Ala
 30                  35                  40                  45

ATC GCT GCC TCG GAC CCC GCC ACC AAG CTC CTA CAG AAG AAT GGT CAG       374
Ile Ala Ala Ser Asp Pro Ala Thr Lys Leu Leu Gln Lys Asn Gly Gln
                 50                  55                  60

CTG TCC ACC ATC AAT GGC GTA GCT GAG CAA GAT GAG CTC AGC CTC CAG       422
Leu Ser Thr Ile Asn Gly Val Ala Glu Gln Asp Glu Leu Ser Leu Gln
             65                  70                  75

GAG GGT GAC CTA AAT GGC CAG AAA GGA GCC CTG AAC GGT CAA GGA GCC       470
Glu Gly Asp Leu Asn Gly Gln Lys Gly Ala Leu Asn Gly Gln Gly Ala
         80                  85                  90

CTA AAC AGC CAG GAG GAA GAA GAA GTC ATT GTC ACG GAG GTT GGA CAG       518
Leu Asn Ser Gln Glu Glu Glu Glu Val Ile Val Thr Glu Val Gly Gln
     95                 100                 105

AGA GAC TCT GAA GAT GTG AGC GAA AGA GAC TCC GAT AAA GAG ATG GCT       566
Arg Asp Ser Glu Asp Val Ser Glu Arg Asp Ser Asp Lys Glu Met Ala
110                 115                 120                 125

ACT AAG TCA GCG GTT GTT CAC GAC ATC ACA GAT GAT GGG CAG GAG GAG       614
Thr Lys Ser Ala Val Val His Asp Ile Thr Asp Asp Gly Gln Glu Glu
                130                 135                 140

AAC CGA AAT ATC GAA CAG ATT CCT TCT TCA GAA AGC AAT TTA GAA GAG       662
```

```
                Asn Arg Asn Ile Glu Gln Ile Pro Ser Ser Glu Ser Asn Leu Glu Glu
                            145                 150                 155

CTA ACA CAA CCC ACT GAG TCC CAG GCT AAT GAT ATT GGA TTT AAG AAG                710
Leu Thr Gln Pro Thr Glu Ser Gln Ala Asn Asp Ile Gly Phe Lys Lys
            160                 165                 170

GTG TTT AAG TTT GTT GGC TTT AAA TTC ACT GTG AAA AAG GAT AAG ACA                758
Val Phe Lys Phe Val Gly Phe Lys Phe Thr Val Lys Lys Asp Lys Thr
175                 180                 185

GAG AAG CCT GAC ACT GTC CAG CTA CTC ACT GTG AAG AAA GAT GAA GGG                806
Glu Lys Pro Asp Thr Val Gln Leu Leu Thr Val Lys Lys Asp Glu Gly
190                 195                 200                 205

GAG GGA GCA GCA GGG GCT GGC GAC CAC CAG GAC CCC AGC CTT GGG GCT                854
Glu Gly Ala Ala Gly Ala Gly Asp His Gln Asp Pro Ser Leu Gly Ala
                210                 215                 220

GGA GAA GCA GCA TCC AAA GAA AGC GAA CCC AAA CAA TCT ACA GAG AAA                902
Gly Glu Ala Ala Ser Lys Glu Ser Glu Pro Lys Gln Ser Thr Glu Lys
            225                 230                 235

CCC GAA GAG ACC CTG AAG CGT GAG CAA AGC CAC GCA GAA ATT TCT CCC                950
Pro Glu Glu Thr Leu Lys Arg Glu Gln Ser His Ala Glu Ile Ser Pro
        240                 245                 250

CCA GCC GAA TCT GGC CAA GCA GTG GAG GAA TGC AAA GAG GAA GGA GAA                998
Pro Ala Glu Ser Gly Gln Ala Val Glu Glu Cys Lys Glu Glu Gly Glu
255                 260                 265

GAG AAA CAA GAA AAA GAA CCT AGC AAG TCT GCA GAA TCT CCG ACT AGT               1046
Glu Lys Gln Glu Lys Glu Pro Ser Lys Ser Ala Glu Ser Pro Thr Ser
270                 275                 280                 285

CCC GTG ACC AGT GAA ACA GGA TCA ACC TTC AAA AAA TTC TTC ACT CAA               1094
Pro Val Thr Ser Glu Thr Gly Ser Thr Phe Lys Lys Phe Phe Thr Gln
                290                 295                 300

GGT TGG GCC GGC TGG CGC AAA AAG ACC AGT TTC AGG AAG CCG AAG GAG               1142
Gly Trp Ala Gly Trp Arg Lys Lys Thr Ser Phe Arg Lys Pro Lys Glu
            305                 310                 315

GAT GAA GTG GAA GCT TCA GAG AAG AAA AAG GAA CAA GAG CCA GAA AAA               1190
Asp Glu Val Glu Ala Ser Glu Lys Lys Lys Glu Gln Glu Pro Glu Lys
        320                 325                 330

GTA GAC ACA GAA GAA GAC GGA AAG GCA GAG GTT GCC TCC GAG AAA CTG               1238
Val Asp Thr Glu Glu Asp Gly Lys Ala Glu Val Ala Ser Glu Lys Leu
335                 340                 345

ACC GCC TCC GAG CAA GCC CAC CCA CAG GAG CCG GCA GAA AGT GCC CAC               1286
Thr Ala Ser Glu Gln Ala His Pro Gln Glu Pro Ala Glu Ser Ala His
350                 355                 360                 365

GAG CCC CGG TTA TCA GCT GAA TAT GAG AAA GTT GAG CTG CCC TCA GAG               1334
Glu Pro Arg Leu Ser Ala Glu Tyr Glu Lys Val Glu Leu Pro Ser Glu
                370                 375                 380

GAG CAA GTC AGT GGC TCG CAG GGA CCT TCT GAA GAG AAA CCT GCT CCG               1382
Glu Gln Val Ser Gly Ser Gln Gly Pro Ser Glu Glu Lys Pro Ala Pro
            385                 390                 395

TTG GCG ACA GAA GTG TTT GAT GAG AAA ATA GAA GTC CAC CAA GAA GAG               1430
Leu Ala Thr Glu Val Phe Asp Glu Lys Ile Glu Val His Gln Glu Glu
        400                 405                 410

GTT GTG GCC GAA GTC CAC GTC AGC ACC GTG GAG GAG AGA ACC GAA GAG               1478
Val Val Ala Glu Val His Val Ser Thr Val Glu Glu Arg Thr Glu Glu
415                 420                 425

CAG AAA ACG GAG GTG GAA GAA ACA GCA GGG TCT GTG CCA GCT GAA GAA               1526
Gln Lys Thr Glu Val Glu Glu Thr Ala Gly Ser Val Pro Ala Glu Glu
430                 435                 440                 445

TTG GTT GGA ATG GAT GCA GAA CCT CAG GAA GCC GAA CCT GCC AAG GAG               1574
Leu Val Gly Met Asp Ala Glu Pro Gln Glu Ala Glu Pro Ala Lys Glu
                450                 455                 460
```

```
CTG GTG AAG CTC AAA GAA ACG TGT GTT TCC GGA GAG GAC CCT ACA CAG     1622
Leu Val Lys Leu Lys Glu Thr Cys Val Ser Gly Glu Asp Pro Thr Gln
            465                 470                 475

GGA GCT GAC CTC AGT CCT GAT GAG AAG GTG CTG TCC AAA CCC CCC GAA     1670
Gly Ala Asp Leu Ser Pro Asp Glu Lys Val Leu Ser Lys Pro Pro Glu
                480                 485                 490

GGC GTT GTG AGT GAG GTG GAA ATG CTG TCA TCA CAG GAG AGA ATG AAG     1718
Gly Val Val Ser Glu Val Glu Met Leu Ser Ser Gln Glu Arg Met Lys
        495                 500                 505

GTG CAG GGA AGT CCA CTA AAG AAG CTT TTT ACC AGC ACT GGC TTA AAA     1766
Val Gln Gly Ser Pro Leu Lys Lys Leu Phe Thr Ser Thr Gly Leu Lys
510                 515                 520                 525

AAG CTT TCT GGA AAG AAA CAG AAA GGG AAA AGA GGA GGA GGA GAC GAG     1814
Lys Leu Ser Gly Lys Lys Gln Lys Gly Lys Arg Gly Gly Gly Asp Glu
                    530                 535                 540

GAA TCA GGG GAG CAC ACT CAG GTT CCA GCC GAT TCT CCG GAC AGC CAG     1862
Glu Ser Gly Glu His Thr Gln Val Pro Ala Asp Ser Pro Asp Ser Gln
                545                 550                 555

GAG GAG CAA AAG GGC GAG AGC TCT GCC TCA TCC CCT GAG GAG CCC GAG     1910
Glu Glu Gln Lys Gly Glu Ser Ser Ala Ser Ser Pro Glu Glu Pro Glu
                560                 565                 570

GAG ATC ACG TGT CTG GAA AAG GGC TTA GCC GAG GTG CAG CAG GAT GGG     1958
Glu Ile Thr Cys Leu Glu Lys Gly Leu Ala Glu Val Gln Gln Asp Gly
                575                 580                 585

GAA GCT GAA GAA GGA GCT ACT TCC GAT GGA GAG AAA AAA AGA GAA GGT     2006
Glu Ala Glu Glu Gly Ala Thr Ser Asp Gly Glu Lys Lys Arg Glu Gly
590                 595                 600                 605

GTC ACT CCC TGG GCA TCA TTC AAA AAG ATG GTG ACG CCC AAG AAG CGT     2054
Val Thr Pro Trp Ala Ser Phe Lys Lys Met Val Thr Pro Lys Lys Arg
                610                 615                 620

GTT AGA CGG CCT TCG GAA AGT GAT AAA GAA GAT GAG CTG GAC AAG GTC     2102
Val Arg Arg Pro Ser Glu Ser Asp Lys Glu Asp Glu Leu Asp Lys Val
                625                 630                 635

AAG AGC GCT ACC TTG TCT TCC ACC GAG AGC ACA GCC TCT GAA ATG CAA     2150
Lys Ser Ala Thr Leu Ser Ser Thr Glu Ser Thr Ala Ser Glu Met Gln
                640                 645                 650

GAA GAA ATG AAA GGG AGC GTG GAA GAG CCA AAG CCG GAA GAA CCA AAG     2198
Glu Glu Met Lys Gly Ser Val Glu Glu Pro Lys Pro Glu Glu Pro Lys
            655                 660                 665

CGC AAG GTG GAT ACC TCA GTA TCT TGG GAA GCT TTA ATT TGT GTG GGA     2246
Arg Lys Val Asp Thr Ser Val Ser Trp Glu Ala Leu Ile Cys Val Gly
670                 675                 680                 685

TCA TCC AAG AAA AGA GCA AGG AGA AGG TCC TCT TCT GAT GAG GAA GGG     2294
Ser Ser Lys Lys Arg Ala Arg Arg Arg Ser Ser Ser Asp Glu Glu Gly
                690                 695                 700

GGA CCA AAA GCA ATG GGA GGA GAC CAC CAG AAA GCT GAT GAG GCC GGA     2342
Gly Pro Lys Ala Met Gly Gly Asp His Gln Lys Ala Asp Glu Ala Gly
                705                 710                 715

AAA GAC AAA GAG ACG GGG ACA GAC GGG ATC CTT GCT GGT TCC CAA GAA     2390
Lys Asp Lys Glu Thr Gly Thr Asp Gly Ile Leu Ala Gly Ser Gln Glu
                720                 725                 730

CAT GAT CCA GGG CAG GGA AGT TCC TCC CCG GAG CAA GCT GGA AGC CCT     2438
His Asp Pro Gly Gln Gly Ser Ser Ser Pro Glu Gln Ala Gly Ser Pro
            735                 740                 745

ACC GAA GGG GAG GGC GTT TCC ACC TGG GAG TCA TTT AAA AGG TTA GTC     2486
Thr Glu Gly Glu Gly Val Ser Thr Trp Glu Ser Phe Lys Arg Leu Val
750                 755                 760                 765

ACG CCA AGA AAA AAA TCA AAG TCC AAG CTG GAA GAG AAA AGC GAA GAC     2534
Thr Pro Arg Lys Lys Ser Lys Ser Lys Leu Glu Glu Lys Ser Glu Asp
                770                 775                 780
```

-continued

| | |
|---|---|
| TCC ATA GCT GGG TCT GGT GTA GAA CAT TCC ACT CCA GAC ACT GAA CCC<br>Ser Ile Ala Gly Ser Gly Val Glu His Ser Thr Pro Asp Thr Glu Pro<br>            785                  790                  795 | 2582 |
| GGT AAA GAA GAA TCC TGG GTC TCA ATC AAG AAG TTT ATT CCT GGA CGA<br>Gly Lys Glu Glu Ser Trp Val Ser Ile Lys Lys Phe Ile Pro Gly Arg<br>            800                  805                  810 | 2630 |
| AGG AAG AAA AGG CCA GAT GGG AAA CAA GAA CAA GCC CCT GTT GAA GAC<br>Arg Lys Lys Arg Pro Asp Gly Lys Gln Glu Gln Ala Pro Val Glu Asp<br>815                  820                  825 | 2678 |
| GCA GGG CCA ACA GGG GCC AAC GAA GAT GAC TCT GAT GTC CCG GCC GTG<br>Ala Gly Pro Thr Gly Ala Asn Glu Asp Asp Ser Asp Val Pro Ala Val<br>830                  835                  840                  845 | 2726 |
| GTC CCT CTG TCT GAG TAT GAT GCT GTA GAA AGG GAG AAA ATG GAG GCA<br>Val Pro Leu Ser Glu Tyr Asp Ala Val Glu Arg Glu Lys Met Glu Ala<br>            850                  855                  860 | 2774 |
| CAG CAA GCC CAA AAA GGC GCA GAG CAG CCC GAG CAG AAG GCA GCC ACT<br>Gln Gln Ala Gln Lys Gly Ala Glu Gln Pro Glu Gln Lys Ala Ala Thr<br>                  865                  870                  875 | 2822 |
| GAG GTG TCC AAG GAG CTC AGC GAG AGT CAG GTT CAT ATG ATG GCA GCA<br>Glu Val Ser Lys Glu Leu Ser Glu Ser Gln Val His Met Met Ala Ala<br>            880                  885                  890 | 2870 |
| GCT GTC GCT GAC GGG ACG AGG GCA GCT ACC ATT ATT GAA GAA AGG TCT<br>Ala Val Ala Asp Gly Thr Arg Ala Ala Thr Ile Ile Glu Glu Arg Ser<br>895                  900                  905 | 2918 |
| CCT TCT TGG ATA TCT GCT TCA GTG ACA GAA CCT CTT GAA CAA GTA GAA<br>Pro Ser Trp Ile Ser Ala Ser Val Thr Glu Pro Leu Glu Gln Val Glu<br>910                  915                  920                  925 | 2966 |
| GCT GAA GCC GCA CTG TTA ACT GAG GAG GTA TTG GAA AGA GAA GTA ATT<br>Ala Glu Ala Ala Leu Leu Thr Glu Glu Val Leu Glu Arg Glu Val Ile<br>                  930                  935                  940 | 3014 |
| GCA GAA GAA GAA CCC CCC ACG GTT ACT GAA CCT CTG CCA GAG AAC AGA<br>Ala Glu Glu Glu Pro Pro Thr Val Thr Glu Pro Leu Pro Glu Asn Arg<br>            945                  950                  955 | 3062 |
| GAG GCC CGG GGC GAC ACG GTC GTT AGT GAG GCG GAA TTG ACC CCC GAA<br>Glu Ala Arg Gly Asp Thr Val Val Ser Glu Ala Glu Leu Thr Pro Glu<br>            960                  965                  970 | 3110 |
| GCT GTG ACA GCT GCA GAA ACT GCA GGG CCA TTG GGT TCC GAA GAA GGA<br>Ala Val Thr Ala Ala Glu Thr Ala Gly Pro Leu Gly Ser Glu Glu Gly<br>975                  980                  985 | 3158 |
| ACC GAA GCA TCT GCT GCT GAA GAG ACC ACA GAA ATG GTG TCA GCA GTC<br>Thr Glu Ala Ser Ala Ala Glu Glu Thr Thr Glu Met Val Ser Ala Val<br>990                  995                  1000              1005 | 3206 |
| TCC CAG TTA ACC GAC TCC CCA GAC ACC ACA GAG GAG GCC ACT CCG GTG<br>Ser Gln Leu Thr Asp Ser Pro Asp Thr Thr Glu Glu Ala Thr Pro Val<br>                  1010                  1015                  1020 | 3254 |
| CAG GAG GTG GAA GGT GGC GTA CCT GAC ATA GAA GAG CAA GAG AGG CGG<br>Gln Glu Val Glu Gly Gly Val Pro Asp Ile Glu Glu Gln Glu Arg Arg<br>            1025                  1030                  1035 | 3302 |
| ACT CAA GAG GTC CTC CAG GCA GTG GCA GAA AAA GTG AAA GAG GAA TCC<br>Thr Gln Glu Val Leu Gln Ala Val Ala Glu Lys Val Lys Glu Glu Ser<br>                  1040                  1045                  1050 | 3350 |
| CAG CTG CCT GGC ACC GGT GGG CCA GAA GAT GTG CTT CAG CCT GTG CAG<br>Gln Leu Pro Gly Thr Gly Gly Pro Glu Asp Val Leu Gln Pro Val Gln<br>            1055                  1060                  1065 | 3398 |
| AGA GCA GAG GCA GAA AGA CCA GAA GAG CAG GCT GAA GCG TCG GGT CTG<br>Arg Ala Glu Ala Glu Arg Pro Glu Glu Gln Ala Glu Ala Ser Gly Leu<br>1070                  1075                  1080                  1085 | 3446 |
| AAG AAA GAG ACG GAT GTA GTG TTG AAA GTA GAT GCT CAG GAG GCA AAA<br>Lys Lys Glu Thr Asp Val Val Leu Lys Val Asp Ala Gln Glu Ala Lys | 3494 |

-continued

```
          1090                1095                1100
ACT GAG CCT TTT ACA CAA GGG AAG GTG GTG GGG CAG ACC ACC CCA GAA    3542
Thr Glu Pro Phe Thr Gln Gly Lys Val Val Gly Gln Thr Thr Pro Glu
            1105                1110                1115

AGC TTT GAA AAA GCT CCT CAA GTC ACA GAG AGC ATA GAG TCC AGT GAG    3590
Ser Phe Glu Lys Ala Pro Gln Val Thr Glu Ser Ile Glu Ser Ser Glu
        1120                1125                1130

CTT GTA ACC ACT TGT CAA GCC GAA ACC TTA GCT GGG GTA AAA TCA CAG    3638
Leu Val Thr Thr Cys Gln Ala Glu Thr Leu Ala Gly Val Lys Ser Gln
        1135                1140                1145

GAG ATG GTG ATG GAA CAG GCT ATC CCC CCT GAC TCG GTG GAA ACC CCT    3686
Glu Met Val Met Glu Gln Ala Ile Pro Pro Asp Ser Val Glu Thr Pro
1150                1155                1160                1165

ACA GAC AGT GAG ACT GAT GGA AGC ACC CCC GTA GCC GAC TTT GAC GCA    3734
Thr Asp Ser Glu Thr Asp Gly Ser Thr Pro Val Ala Asp Phe Asp Ala
                1170                1175                1180

CCA GGC ACA ACC CAG AAA GAC GAG ATT GTG GAA ATC CAT GAG GAG AAT    3782
Pro Gly Thr Thr Gln Lys Asp Glu Ile Val Glu Ile His Glu Glu Asn
            1185                1190                1195

GAG GTG CAT CTG GTA CCA GTC AGG GGC ACA GAA GCA GAG GCA GTT CCT    3830
Glu Val His Leu Val Pro Val Arg Gly Thr Glu Ala Glu Ala Val Pro
        1200                1205                1210

GCA CAG AAA GAG AGG CCT CCA GCA CCT TCC AGT TTT GTG TTC CAG GAA    3878
Ala Gln Lys Glu Arg Pro Pro Ala Pro Ser Ser Phe Val Phe Gln Glu
    1215                1220                1225

GAA ACT AAA GAA CAA TCA AAG ATG GAA GAC ACT CTA GAG CAT ACA GAT    3926
Glu Thr Lys Glu Gln Ser Lys Met Glu Asp Thr Leu Glu His Thr Asp
1230                1235                1240                1245

AAA GAG GTG TCA GTG GAA ACT GTA TCC ATT CTG TCA AAG ACT GAG GGG    3974
Lys Glu Val Ser Val Glu Thr Val Ser Ile Leu Ser Lys Thr Glu Gly
                1250                1255                1260

ACT CAA GAG GCT GAC CAG TAT GCT GAT GAG AAA ACC AAA GAC GTA CCA    4022
Thr Gln Glu Ala Asp Gln Tyr Ala Asp Glu Lys Thr Lys Asp Val Pro
            1265                1270                1275

TTT TTC GAA GGA CTT GAG GGG TCT ATA GAC ACA GGC ATA ACA GTC AGT    4070
Phe Phe Glu Gly Leu Glu Gly Ser Ile Asp Thr Gly Ile Thr Val Ser
        1280                1285                1290

CGG GAA AAG GTC ACT GAA GTT GCC CTT AAA GGT GAA GGG ACA GAA GAA    4118
Arg Glu Lys Val Thr Glu Val Ala Leu Lys Gly Glu Gly Thr Glu Glu
    1295                1300                1305

GCT GAA TGT AAA AAG GAT GAT GCT CTT GAA CTG CAG AGT CAC GCT AAG    4166
Ala Glu Cys Lys Lys Asp Asp Ala Leu Glu Leu Gln Ser His Ala Lys
1310                1315                1320                1325

TCT CCT CCA TCC CCC GTG GAG AGA GAG ATG GTA GTT CAA GTC GAA AGG    4214
Ser Pro Pro Ser Pro Val Glu Arg Glu Met Val Val Gln Val Glu Arg
                1330                1335                1340

GAG AAA ACA GAA GCA GAG CCA ACC CAT GTG AAT GAA GAG AAG CTT GAG    4262
Glu Lys Thr Glu Ala Glu Pro Thr His Val Asn Glu Glu Lys Leu Glu
            1345                1350                1355

CAC GAA ACA GCT GTT ACC GTA TCT GAA GAG GTC AGT AAG CAG CTC CTC    4310
His Glu Thr Ala Val Thr Val Ser Glu Glu Val Ser Lys Gln Leu Leu
        1360                1365                1370

CAG ACA GTG AAT GTG CCC ATC ATA GAT GGG GCA AAG GAA GTC AGC AGT    4358
Gln Thr Val Asn Val Pro Ile Ile Asp Gly Ala Lys Glu Val Ser Ser
    1375                1380                1385

TTG GAA GGA AGC CCT CCT CCC TGC CTA GGT CAA GAG GAG GCA GTA TGC    4406
Leu Glu Gly Ser Pro Pro Pro Cys Leu Gly Gln Glu Glu Ala Val Cys
1390                1395                1400                1405

ACC AAA ATT CAA GTT CAG AGC TCT GAG GCA TCA TTC ACT CTA ACA GCG    4454
```

-continued

```
Thr Lys Ile Gln Val Gln Ser Ser Glu Ala Ser Phe Thr Leu Thr Ala
            1410                1415                1420

GCT GCA GAG GAG GAA AAG GTC TTA GGA GAA ACT GCC AAC ATT TTA GAA      4502
Ala Ala Glu Glu Glu Lys Val Leu Gly Glu Thr Ala Asn Ile Leu Glu
            1425                1430                1435

ACA GGT GAA ACG TTG GAG CCT GCA GGT GCA CAT TTA GTT CTG GAA GAG      4550
Thr Gly Glu Thr Leu Glu Pro Ala Gly Ala His Leu Val Leu Glu Glu
            1440                1445                1450

AAA TCC TCT GAA AAA AAT GAA GAC TTT GCC GCT CAT CCA GGG GAA GAT      4598
Lys Ser Ser Glu Lys Asn Glu Asp Phe Ala Ala His Pro Gly Glu Asp
            1455                1460                1465

GCT GTG CCC ACA GGG CCC GAC TGT CAG GCA AAA TCG ACA CCA GTG ATA      4646
Ala Val Pro Thr Gly Pro Asp Cys Gln Ala Lys Ser Thr Pro Val Ile
1470                1475                1480                1485

GTA TCT GCT ACT ACC AAG AAA GGC TTA AGT TCC GAC CTG GAA GGA GAG      4694
Val Ser Ala Thr Thr Lys Lys Gly Leu Ser Ser Asp Leu Glu Gly Glu
            1490                1495                1500

AAA ACC ACA TCA CTG AAG TGG AAG TCA GAT GAA GTC GAT GAG CAG GTT      4742
Lys Thr Thr Ser Leu Lys Trp Lys Ser Asp Glu Val Asp Glu Gln Val
            1505                1510                1515

GCT TGC CAG GAG GTC AAA GTG AGT GTA GCA ATT GAG GAT TTA GAG CCT      4790
Ala Cys Gln Glu Val Lys Val Ser Val Ala Ile Glu Asp Leu Glu Pro
            1520                1525                1530

GAA AAT GGG ATT TTG GAA CTT GAG ACC AAA AGC AGT AAA CTT GTC CAA      4838
Glu Asn Gly Ile Leu Glu Leu Glu Thr Lys Ser Ser Lys Leu Val Gln
            1535                1540                1545

AAC ATC ATC CAG ACA GCC GTT GAC CAG TTT GTA CGT ACA GAA GAA ACA      4886
Asn Ile Ile Gln Thr Ala Val Asp Gln Phe Val Arg Thr Glu Glu Thr
1550                1555                1560                1565

GCC ACC GAA ATG TTG ACG TCT GAG TTA CAG ACA CAA GCT CAC GTG ATA      4934
Ala Thr Glu Met Leu Thr Ser Glu Leu Gln Thr Gln Ala His Val Ile
            1570                1575                1580

AAA GCT GAC AGC CAG GAC GCT GGA CAG GAA ACG GAG AAA GAA GGA GAG      4982
Lys Ala Asp Ser Gln Asp Ala Gly Gln Glu Thr Glu Lys Glu Gly Glu
            1585                1590                1595

GAA CCT CAG GCC TCT GCA CAG GAT GAA ACA CCA ATT ACT TCA GCC AAA      5030
Glu Pro Gln Ala Ser Ala Gln Asp Glu Thr Pro Ile Thr Ser Ala Lys
            1600                1605                1610

GAG GAG TCA GAG TCA ACC GCA GTG GGA CAA GCA CAT TCT GAT ATT TCC      5078
Glu Glu Ser Glu Ser Thr Ala Val Gly Gln Ala His Ser Asp Ile Ser
            1615                1620                1625

AAA GAC ATG AGT GAA GCC TCA GAA AAG ACC ATG ACT GTT GAG GTA GAA      5126
Lys Asp Met Ser Glu Ala Ser Glu Lys Thr Met Thr Val Glu Val Glu
1630                1635                1640                1645

GGT TCC ACT GTA AAT GAT CAG CAG CTG GAA GAG GTC GTC CTC CCA TCT      5174
Gly Ser Thr Val Asn Asp Gln Gln Leu Glu Glu Val Val Leu Pro Ser
            1650                1655                1660

GAG GAA GAG GGA GGT GGA GCT GGA ACA AAG TCT GTG CCA GAA GAT GAT      5222
Glu Glu Glu Gly Gly Gly Ala Gly Thr Lys Ser Val Pro Glu Asp Asp
            1665                1670                1675

GGT CAT GCC TTG TTA GCA GAA AGA ATA GAG AAG TCA CTA GTT GAA CCG      5270
Gly His Ala Leu Leu Ala Glu Arg Ile Glu Lys Ser Leu Val Glu Pro
            1680                1685                1690

AAA GAA GAT GAA AAA GGT GAT GAT GTT GAT GAC CCT GAA AAC CAG AAC      5318
Lys Glu Asp Glu Lys Gly Asp Asp Val Asp Asp Pro Glu Asn Gln Asn
            1695                1700                1705

TCA GCC CTG GCT GAT ACT GAT GCC TCA GGA GGC TTA ACC AAA GAG TCC      5366
Ser Ala Leu Ala Asp Thr Asp Ala Ser Gly Gly Leu Thr Lys Glu Ser
1710                1715                1720                1725
```

```
CCA GAT ACA AAT GGA CCA AAA CAA AAA GAG AAG GAG GAT GCC CAG GAA       5414
Pro Asp Thr Asn Gly Pro Lys Gln Lys Glu Lys Glu Asp Ala Gln Glu
                    1730                1735                1740

GTA GAA TTG CAG GAA GGA AAA GTG CAC AGT GAA TCA GAT AAA GCG ATC       5462
Val Glu Leu Gln Glu Gly Lys Val His Ser Glu Ser Asp Lys Ala Ile
            1745                1750                1755

ACA CCC CAA GCA CAG GAG GAG TTA CAG AAA CAA GAG AGA GAA TCT GCA       5510
Thr Pro Gln Ala Gln Glu Glu Leu Gln Lys Gln Glu Arg Glu Ser Ala
        1760                1765                1770

AAG TCA GAA CTT ACA GAA TCT TAAAACATCA TGCAGTTAAA CTCATTGTCT          5561
Lys Ser Glu Leu Thr Glu Ser
    1775            1780

GTTTGGAAGA CCAGAATGTG AAGACAAGTA GTAGAAGAAA ATGAATGCTG CTGCTGAGAC     5621

TGAAGACCAG TATTTCAGAA CTTTGAGAAT GGAGAGCAG GCACATCAAC TGATCTCATT      5681

TCTAGAGAGC CCCTGACAAT CCTGAGGCTT CATCAGGAGC TAGAGCCATT TAACATTTCC     5741

TCTTTCCAAG ACCAACCTAC AATTTTCCCT TGATAACCAT ATAAATTCTG ATTTAAGGTC     5801

CTAAATTCTT AACCTGGAAC TGGAGTTGGC AATACCTAGT TCTGCTTCTG AAACTGGAGT     5861

ATCATTCTTT ACATATTTAT ATGTATGTTT TAAGTAGTCC TCCTGTATCT ATTGTATATT     5921

TTTTTCTTAA TGTTTAAGGA AATGTGCAGG ATACTACATG CTTTTTGTAT CACACAGTAT     5981

ATGATGGGGC ATGTGCCATA GTGCAGGCTT GGGGAGCTTT AAGCCTCAGT TATATAACCC     6041

ACAAAAAACA GAGCCTCCTA GATGTAACAT TCCTGATCAA GGTACAATTC TTTAAAATTC     6101

ACTAATGATT GAGGTCCATA TTTAGTGGTA CTCTGAAATT GGTCACTTTC CTATTACACG     6161

GAGTGTGCCA AAACTAAAAA GCATTTTGAA ACATACAGAA TGTTCTATTG TCATTGGGAA     6221

ATTTTGCTTT CTAACCCAGT GGAGGTTAGA AAGAAGTTAT ATTCTGGTAG CAAATTAACT     6281

TTACATCCTT TTTCCTACTT GTTATGGTTG TTTGGACCGA TAAGTGTGCT TAATCCTGAG     6341

GCAAAGTAGT GAATATGTTT TATATGTTAT GAAGAAAAGA ATTGTTGTAA GTTTTTGATT     6401

CTACTCTTAT ATGCTGGACT GCATTCACAC ATGGCATGAA ATAAGTCAGG TTCTTTACAA     6461

ATGGTATTTT GATAGATACT GGATTGTGTT TGTGCCATAT TTGTGCCATT CCTTTAAGAA     6521

CAATGTTGCA ACACATTCAT TTGGATAAGT TGTGATTTGA CGACTGATTT AAATAAAATA     6581

TTTGCTTCAC TTAAAAAAAA AAAA                                            6605

(2) INFORMATION FOR SEQ ID NO:5:

(i) SEQUENCE CHARACTERISTICS:
        (A) LENGTH: 1780 amino acids
        (B) TYPE: amino acid
        (D) TOPOLOGY: linear (ii) MOLECULE TYPE: protein (xi) SEQUENCE DESCRIPTION: SEQ ID NO:5:

Met Gly Ala Gly Ser Ser Thr Glu Gln Arg Ser Pro Glu Gln Pro Pro
 1               5                  10                  15

Glu Gly Ser Ser Thr Pro Ala Gly Pro Glu Pro Ser Gly Gly Gly Pro
            20                  25                  30

Ser Ala Glu Ala Ala Pro Asp Thr Thr Ala Asp Pro Ala Ile Ala Ala
        35                  40                  45

Ser Asp Pro Ala Thr Lys Leu Leu Gln Lys Asn Gly Gln Leu Ser Thr
    50                  55                  60

Ile Asn Gly Val Ala Glu Gln Asp Glu Leu Ser Leu Gln Glu Gly Asp
65                  70                  75                  80
```

-continued

```
Leu Asn Gly Gln Lys Gly Ala Leu Asn Gly Gln Gly Ala Leu Asn Ser
                 85                  90                  95
Gln Glu Glu Glu Val Ile Val Thr Glu Val Gly Gln Arg Asp Ser
            100                 105                 110
Glu Asp Val Ser Glu Arg Asp Ser Asp Lys Glu Met Ala Thr Lys Ser
            115                 120                 125
Ala Val Val His Asp Ile Thr Asp Asp Gly Gln Glu Glu Asn Arg Asn
            130                 135                 140
Ile Glu Gln Ile Pro Ser Ser Glu Ser Asn Leu Glu Glu Leu Thr Gln
145                 150                 155                 160
Pro Thr Glu Ser Gln Ala Asn Asp Ile Gly Phe Lys Lys Val Phe Lys
                165                 170                 175
Phe Val Gly Phe Lys Phe Thr Val Lys Lys Asp Lys Thr Glu Lys Pro
            180                 185                 190
Asp Thr Val Gln Leu Leu Thr Val Lys Lys Asp Glu Gly Glu Gly Ala
            195                 200                 205
Ala Gly Ala Gly Asp His Gln Asp Pro Ser Leu Gly Ala Gly Glu Ala
            210                 215                 220
Ala Ser Lys Glu Ser Glu Pro Lys Gln Ser Thr Glu Lys Pro Glu Glu
225                 230                 235                 240
Thr Leu Lys Arg Glu Gln Ser His Ala Glu Ile Ser Pro Pro Ala Glu
                245                 250                 255
Ser Gly Gln Ala Val Glu Glu Cys Lys Glu Gly Glu Glu Lys Gln
            260                 265                 270
Glu Lys Glu Pro Ser Lys Ser Ala Glu Ser Pro Thr Ser Pro Val Thr
            275                 280                 285
Ser Glu Thr Gly Ser Thr Phe Lys Lys Phe Phe Thr Gln Gly Trp Ala
            290                 295                 300
Gly Trp Arg Lys Lys Thr Ser Phe Arg Lys Pro Lys Glu Asp Glu Val
305                 310                 315                 320
Glu Ala Ser Glu Lys Lys Lys Glu Gln Glu Pro Glu Lys Val Asp Thr
            325                 330                 335
Glu Glu Asp Gly Lys Ala Glu Val Ala Ser Glu Lys Leu Thr Ala Ser
            340                 345                 350
Glu Gln Ala His Pro Gln Glu Pro Ala Glu Ser Ala His Glu Pro Arg
            355                 360                 365
Leu Ser Ala Glu Tyr Glu Lys Val Glu Leu Pro Ser Glu Glu Gln Val
            370                 375                 380
Ser Gly Ser Gln Gly Pro Ser Glu Glu Lys Pro Ala Pro Leu Ala Thr
385                 390                 395                 400
Glu Val Phe Asp Glu Lys Ile Glu Val His Gln Glu Val Ala
                405                 410                 415
Glu Val His Val Ser Thr Val Glu Glu Arg Thr Glu Glu Gln Lys Thr
            420                 425                 430
Glu Val Glu Glu Thr Ala Gly Ser Val Pro Ala Glu Glu Leu Val Gly
            435                 440                 445
Met Asp Ala Glu Pro Gln Glu Ala Glu Pro Ala Lys Glu Leu Val Lys
            450                 455                 460
Leu Lys Glu Thr Cys Val Ser Gly Glu Asp Pro Thr Gln Gly Ala Asp
465                 470                 475                 480
Leu Ser Pro Asp Glu Lys Val Leu Ser Lys Pro Pro Glu Gly Val Val
                485                 490                 495
Ser Glu Val Glu Met Leu Ser Ser Gln Glu Arg Met Lys Val Gln Gly
```

-continued

```
                500                 505                 510
Ser Pro Leu Lys Lys Leu Phe Thr Ser Thr Gly Leu Lys Lys Leu Ser
            515                 520                 525
Gly Lys Lys Gln Lys Gly Lys Arg Gly Gly Asp Glu Glu Ser Gly
    530                 535                 540
Glu His Thr Gln Val Pro Ala Asp Ser Pro Asp Ser Gln Glu Glu Gln
545                 550                 555                 560
Lys Gly Glu Ser Ser Ala Ser Ser Pro Glu Glu Pro Glu Glu Ile Thr
                565                 570                 575
Cys Leu Glu Lys Gly Leu Ala Glu Val Gln Gln Asp Gly Glu Ala Glu
            580                 585                 590
Glu Gly Ala Thr Ser Asp Gly Glu Lys Lys Arg Glu Gly Val Thr Pro
        595                 600                 605
Trp Ala Ser Phe Lys Lys Met Val Thr Pro Lys Lys Arg Val Arg Arg
    610                 615                 620
Pro Ser Glu Ser Asp Lys Glu Asp Glu Leu Asp Lys Val Lys Ser Ala
625                 630                 635                 640
Thr Leu Ser Ser Thr Glu Ser Thr Ala Ser Glu Met Gln Glu Glu Met
                645                 650                 655
Lys Gly Ser Val Glu Glu Pro Lys Pro Glu Glu Pro Lys Arg Lys Val
            660                 665                 670
Asp Thr Ser Val Ser Trp Glu Ala Leu Ile Cys Val Gly Ser Ser Lys
        675                 680                 685
Lys Arg Ala Arg Arg Ser Ser Asp Glu Glu Gly Gly Pro Lys
    690                 695                 700
Ala Met Gly Gly Asp His Gln Lys Ala Asp Glu Ala Gly Lys Asp Lys
705                 710                 715                 720
Glu Thr Gly Thr Asp Gly Ile Leu Ala Gly Ser Gln Glu His Asp Pro
                725                 730                 735
Gly Gln Gly Ser Ser Pro Glu Gln Ala Gly Ser Pro Thr Glu Gly
            740                 745                 750
Glu Gly Val Ser Thr Trp Glu Ser Phe Lys Arg Leu Val Thr Pro Arg
        755                 760                 765
Lys Lys Ser Lys Ser Lys Leu Glu Glu Lys Ser Glu Asp Ser Ile Ala
    770                 775                 780
Gly Ser Gly Val Glu His Ser Thr Pro Asp Thr Glu Pro Gly Lys Glu
785                 790                 795                 800
Glu Ser Trp Val Ser Ile Lys Lys Phe Ile Pro Gly Arg Arg Lys Lys
                805                 810                 815
Arg Pro Asp Gly Lys Gln Glu Gln Ala Pro Val Glu Asp Ala Gly Pro
            820                 825                 830
Thr Gly Ala Asn Glu Asp Asp Ser Asp Val Pro Ala Val Pro Leu
        835                 840                 845
Ser Glu Tyr Asp Ala Val Glu Arg Glu Lys Met Glu Ala Gln Gln Ala
    850                 855                 860
Gln Lys Gly Ala Glu Gln Pro Glu Gln Lys Ala Ala Thr Glu Val Ser
865                 870                 875                 880
Lys Glu Leu Ser Glu Ser Gln Val His Met Met Ala Ala Ala Val Ala
                885                 890                 895
Asp Gly Thr Arg Ala Ala Thr Ile Ile Glu Glu Arg Ser Pro Ser Trp
            900                 905                 910
Ile Ser Ala Ser Val Thr Glu Pro Leu Glu Gln Val Glu Ala Glu Ala
        915                 920                 925
```

-continued

Ala Leu Leu Thr Glu Val Leu Glu Arg Glu Val Ile Ala Glu Glu
        930                 935                 940

Glu Pro Pro Thr Val Thr Glu Pro Leu Pro Glu Asn Arg Glu Ala Arg
945                 950                 955                 960

Gly Asp Thr Val Val Ser Glu Ala Glu Leu Thr Pro Glu Ala Val Thr
                965                 970                 975

Ala Ala Glu Thr Ala Gly Pro Leu Gly Ser Glu Gly Thr Glu Ala
        980                 985                 990

Ser Ala Ala Glu Glu Thr Thr Glu Met Val Ser Ala Val Ser Gln Leu
        995                 1000                1005

Thr Asp Ser Pro Asp Thr Thr Glu Glu Ala Thr Pro Val Gln Glu Val
    1010                1015                1020

Glu Gly Gly Val Pro Asp Ile Glu Glu Gln Glu Arg Arg Thr Gln Glu
1025                1030                1035                1040

Val Leu Gln Ala Val Ala Glu Lys Val Lys Glu Ser Gln Leu Pro
            1045                1050                1055

Gly Thr Gly Gly Pro Glu Asp Val Leu Gln Pro Val Gln Arg Ala Glu
            1060                1065                1070

Ala Glu Arg Pro Glu Glu Gln Ala Glu Ala Ser Gly Leu Lys Lys Glu
        1075                1080                1085

Thr Asp Val Val Leu Lys Val Asp Ala Gln Glu Ala Lys Thr Glu Pro
    1090                1095                1100

Phe Thr Gln Gly Lys Val Val Gly Gln Thr Thr Pro Glu Ser Phe Glu
1105                1110                1115                1120

Lys Ala Pro Gln Val Thr Glu Ser Ile Glu Ser Ser Glu Leu Val Thr
            1125                1130                1135

Thr Cys Gln Ala Glu Thr Leu Ala Gly Val Lys Ser Gln Glu Met Val
        1140                1145                1150

Met Glu Gln Ala Ile Pro Pro Asp Ser Val Glu Thr Pro Thr Asp Ser
        1155                1160                1165

Glu Thr Asp Gly Ser Thr Pro Val Ala Asp Phe Asp Ala Pro Gly Thr
        1170                1175                1180

Thr Gln Lys Asp Glu Ile Val Glu Ile His Glu Glu Asn Glu Val His
1185                1190                1195                1200

Leu Val Pro Val Arg Gly Thr Glu Ala Glu Ala Val Pro Ala Gln Lys
            1205                1210                1215

Glu Arg Pro Pro Ala Pro Ser Ser Phe Val Phe Gln Glu Glu Thr Lys
        1220                1225                1230

Glu Gln Ser Lys Met Glu Asp Thr Leu Glu His Thr Asp Lys Glu Val
        1235                1240                1245

Ser Val Glu Thr Val Ser Ile Leu Ser Lys Thr Glu Gly Thr Gln Glu
    1250                1255                1260

Ala Asp Gln Tyr Ala Asp Glu Lys Thr Lys Asp Val Pro Phe Phe Glu
1265                1270                1275                1280

Gly Leu Glu Gly Ser Ile Asp Thr Gly Ile Thr Val Ser Arg Glu Lys
                1285                1290                1295

Val Thr Glu Val Ala Leu Lys Gly Glu Gly Thr Glu Glu Ala Glu Cys
        1300                1305                1310

Lys Lys Asp Asp Ala Leu Glu Leu Gln Ser His Ala Lys Ser Pro Pro
    1315                1320                1325

Ser Pro Val Glu Arg Glu Met Val Val Gln Val Glu Arg Glu Lys Thr
    1330                1335                1340

```
Glu Ala Glu Pro Thr His Val Asn Glu Glu Lys Leu Glu His Glu Thr
1345                1350                1355                1360

Ala Val Thr Val Ser Glu Glu Val Ser Lys Gln Leu Leu Gln Thr Val
            1365                1370                1375

Asn Val Pro Ile Ile Asp Gly Ala Lys Glu Val Ser Ser Leu Glu Gly
            1380                1385                1390

Ser Pro Pro Cys Leu Gly Gln Glu Glu Ala Val Cys Thr Lys Ile
        1395                1400                1405

Gln Val Gln Ser Ser Glu Ala Ser Phe Thr Leu Thr Ala Ala Ala Glu
        1410                1415                1420

Glu Glu Lys Val Leu Gly Glu Thr Ala Asn Ile Leu Glu Thr Gly Glu
1425                1430                1435                1440

Thr Leu Glu Pro Ala Gly Ala His Leu Val Leu Glu Glu Lys Ser Ser
                1445                1450                1455

Glu Lys Asn Glu Asp Phe Ala Ala His Pro Gly Glu Asp Ala Val Pro
            1460                1465                1470

Thr Gly Pro Asp Cys Gln Ala Lys Ser Thr Pro Val Ile Val Ser Ala
            1475                1480                1485

Thr Thr Lys Lys Gly Leu Ser Ser Asp Leu Glu Gly Glu Lys Thr Thr
        1490                1495                1500

Ser Leu Lys Trp Lys Ser Asp Glu Val Asp Glu Gln Val Ala Cys Gln
1505                1510                1515                1520

Glu Val Lys Val Ser Val Ala Ile Glu Asp Leu Glu Pro Glu Asn Gly
            1525                1530                1535

Ile Leu Glu Leu Glu Thr Lys Ser Ser Lys Leu Val Gln Asn Ile Ile
                1540                1545                1550

Gln Thr Ala Val Asp Gln Phe Val Arg Thr Glu Glu Thr Ala Thr Glu
        1555                1560                1565

Met Leu Thr Ser Glu Leu Gln Thr Gln Ala His Val Ile Lys Ala Asp
        1570                1575                1580

Ser Gln Asp Ala Gly Gln Glu Thr Glu Lys Glu Gly Glu Glu Pro Gln
1585                1590                1595                1600

Ala Ser Ala Gln Asp Glu Thr Pro Ile Thr Ser Ala Lys Glu Glu Ser
            1605                1610                1615

Glu Ser Thr Ala Val Gly Gln Ala His Ser Asp Ile Ser Lys Asp Met
            1620                1625                1630

Ser Glu Ala Ser Glu Lys Thr Met Thr Val Glu Val Glu Gly Ser Thr
        1635                1640                1645

Val Asn Asp Gln Gln Leu Glu Glu Val Val Leu Pro Ser Glu Glu Glu
    1650                1655                1660

Gly Gly Gly Ala Gly Thr Lys Ser Val Pro Glu Asp Asp Gly His Ala
1665                1670                1675                1680

Leu Leu Ala Glu Arg Ile Glu Lys Ser Leu Val Glu Pro Lys Glu Asp
                1685                1690                1695

Glu Lys Gly Asp Asp Val Asp Asp Pro Glu Asn Gln Asn Ser Ala Leu
            1700                1705                1710

Ala Asp Thr Asp Ala Ser Gly Gly Leu Thr Lys Glu Ser Pro Asp Thr
            1715                1720                1725

Asn Gly Pro Lys Gln Lys Glu Lys Glu Asp Ala Gln Glu Val Glu Leu
        1730                1735                1740

Gln Glu Gly Lys Val His Ser Glu Ser Asp Lys Ala Ile Thr Pro Gln
1745                1750                1755                1760

Ala Gln Glu Glu Leu Gln Lys Gln Glu Arg Glu Ser Ala Lys Ser Glu
```

```
                   1765                1770                1775
Leu Thr Glu Ser
          1780

(2) INFORMATION FOR SEQ ID NO:6:

(i) SEQUENCE CHARACTERISTICS:
         (A) LENGTH: 14 amino acids
         (B) TYPE: amino acid
         (C) STRANDEDNESS: single
         (D) TOPOLOGY: linear (xi) SEQUENCE DESCRIPTION: SEQ ID NO:6:

Leu Glu Thr Lys Ser Ser Lys Leu Val Gln Asn Ile Ile Gln
1               5                   10

(2) INFORMATION FOR SEQ ID NO:7:

(i) SEQUENCE CHARACTERISTICS:
         (A) LENGTH: 14 amino acids
         (B) TYPE: amino acid
         (C) STRANDEDNESS: single
         (D) TOPOLOGY: linear (xi) SEQUENCE DESCRIPTION: SEQ ID NO:7:

Leu Ile Glu Thr Ala Ser Ser Leu Val Lys Asn Ala Ile Gln
1               5                   10

(2) INFORMATION FOR SEQ ID NO:8:

(i) SEQUENCE CHARACTERISTICS:
         (A) LENGTH: 23 amino acids
         (B) TYPE: amino acid
         (C) STRANDEDNESS: single
         (D) TOPOLOGY: linear (xi) SEQUENCE DESCRIPTION: SEQ ID NO:8:

Asp Leu Ile Glu Glu Ala Ala Ser Arg Ile Val Asp Ala Val Ile
1               5                   10                  15

Glu Gln Val Lys Ala Ala Gly Ala
                20

(2) INFORMATION FOR SEQ ID NO:9:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (xi) SEQUENCE DESCRIPTION: SEQ ID NO:9:

CCGCCATGGT GCATATGTCC GAGTCCAGTG AGC                              33

(2) INFORMATION FOR SEQ ID NO:10:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (xi) SEQUENCE DESCRIPTION: SEQ ID NO:10:

GCGCGGATCC GCACTCACTT TGACCTCCTG                                  30

(2) INFORMATION FOR SEQ ID NO:11:
```

(i) SEQUENCE CHARACTERISTICS:
    (A) LENGTH: 30 base pairs
    (B) TYPE: nucleic acid
    (C) STRANDEDNESS: single
    (D) TOPOLOGY: linear (xi) SEQUENCE DESCRIPTION: SEQ ID NO:11:

GCGCGGATCC GCTATCACGT GAGCTTGTGT                                    30

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:12:

CCGCCATGGT GCATATGGTA GCAATTGAGG ATTTAG                              36

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:13:

GGAGGATCCA GAGATTCTGT AGTTCTG                                        27

(2) INFORMATION FOR SEQ ID NO:14:

(i) SEQUENCE CHARACTERISTICS:
        (A) LENGTH: 453 amino acids
        (B) TYPE: amino acid
        (C) STRANDEDNESS: single
        (D) TOPOLOGY: linear (xi) SEQUENCE DESCRIPTION: SEQ ID NO:14:

Glu Ser Ser Glu Leu Val Thr Thr Cys Gln Ala Glu Thr Leu Ala Gly
1               5                   10                  15

Val Lys Ser Gln Glu Met Val Met Gln Ala Ile Pro Pro Asp Ser
            20                  25                  30

Val Glu Thr Pro Thr Asp Ser Glu Thr Asp Gly Ser Thr Pro Val Ala
            35                  40                  45

Asp Phe Asp Ala Pro Gly Thr Thr Gln Lys Asp Glu Ile Val Glu Ile
        50                  55                  60

His Glu Glu Asn Glu Val His Leu Val Pro Val Arg Gly Thr Glu Ala
65                  70                  75                  80

Glu Ala Val Pro Ala Gln Lys Glu Arg Pro Ala Pro Ser Ser Phe
            85                  90                  95

Val Phe Gln Glu Glu Thr Lys Glu Gln Ser Lys Met Glu Asp Thr Leu
            100                 105                 110

Glu His Thr Asp Lys Glu Val Ser Val Glu Thr Val Ser Ile Leu Ser
            115                 120                 125

Lys Thr Glu Gly Thr Gln Glu Ala Asp Gln Tyr Ala Asp Glu Lys Thr
        130                 135                 140

Lys Asp Val Pro Phe Phe Glu Gly Leu Glu Gly Ser Ile Asp Thr Gly
145                 150                 155                 160

Ile Thr Val Ser Arg Glu Lys Val Thr Glu Val Ala Leu Lys Gly Glu
                165                 170                 175

```
Gly Thr Glu Glu Ala Glu Cys Lys Lys Asp Asp Ala Leu Glu Leu Gln
            180                 185                 190

Ser His Ala Lys Ser Pro Pro Ser Pro Val Glu Arg Glu Met Val Val
            195                 200                 205

Gln Val Glu Arg Glu Lys Thr Glu Ala Glu Pro Thr His Val Asn Glu
            210                 215                 220

Glu Lys Leu Glu His Glu Thr Ala Val Thr Val Ser Glu Glu Val Ser
225                 230                 235                 240

Lys Gln Leu Leu Gln Thr Val Asn Val Pro Ile Ile Asp Gly Ala Lys
            245                 250                 255

Glu Val Ser Ser Leu Glu Gly Ser Pro Pro Cys Leu Gly Gln Glu
            260                 265                 270

Glu Ala Val Cys Thr Lys Ile Gln Val Gln Ser Ser Glu Ala Ser Phe
            275                 280                 285

Thr Leu Thr Ala Ala Ala Glu Glu Lys Val Leu Gly Glu Thr Ala
            290                 295                 300

Asn Ile Leu Glu Thr Gly Glu Thr Leu Glu Pro Ala Gly Ala His Leu
305                 310                 315                 320

Val Leu Glu Glu Lys Ser Ser Glu Lys Asn Glu Asp Phe Ala Ala His
            325                 330                 335

Pro Gly Glu Asp Ala Val Pro Thr Gly Pro Asp Cys Gln Ala Lys Ser
            340                 345                 350

Thr Pro Val Ile Val Ser Ala Thr Thr Lys Lys Gly Leu Ser Ser Asp
            355                 360                 365

Leu Glu Gly Glu Lys Thr Thr Ser Leu Lys Trp Lys Ser Asp Glu Val
370                 375                 380

Asp Glu Gln Val Ala Cys Gln Glu Val Lys Val Ser Val Ala Ile Glu
385                 390                 395                 400

Asp Leu Glu Pro Glu Asn Gly Ile Leu Glu Leu Glu Thr Lys Ser Ser
            405                 410                 415

Lys Leu Val Gln Asn Ile Ile Gln Thr Ala Val Asp Gln Phe Val Arg
            420                 425                 430

Thr Glu Glu Thr Ala Thr Glu Met Leu Thr Ser Glu Leu Gln Thr Gln
            435                 440                 445

Ala His Val Ile Lys
        450

(2) INFORMATION FOR SEQ ID NO:15:

(i) SEQUENCE CHARACTERISTICS:
        (A) LENGTH: 396 amino acids
        (B) TYPE: amino acid
        (C) STRANDEDNESS: single
        (D) TOPOLOGY: linear (xi) SEQUENCE DESCRIPTION: SEQ ID NO:15:

Glu Ser Ser Glu Leu Val Thr Thr Cys Gln Ala Glu Thr Leu Ala Gly
1               5                   10                  15

Val Lys Ser Gln Glu Met Val Met Glu Gln Ala Ile Pro Pro Asp Ser
            20                  25                  30

Val Glu Thr Pro Thr Asp Ser Glu Thr Asp Gly Ser Thr Pro Val Ala
            35                  40                  45

Asp Phe Asp Ala Pro Gly Thr Thr Gln Lys Asp Glu Ile Val Glu Ile
            50                  55                  60

His Glu Glu Asn Glu Val His Leu Val Pro Val Arg Gly Thr Glu Ala
```

-continued

```
              65                  70                  75                  80
Glu Ala Val Pro Ala Gln Lys Glu Arg Pro Ala Pro Ser Ser Phe
                    85                  90                  95
Val Phe Gln Glu Glu Thr Lys Glu Gln Ser Lys Met Glu Asp Thr Leu
                100                 105                 110
Glu His Thr Asp Lys Glu Val Ser Val Glu Thr Val Ser Ile Leu Ser
                115                 120                 125
Lys Thr Glu Gly Thr Gln Glu Ala Asp Gln Tyr Ala Asp Glu Lys Thr
            130                 135                 140
Lys Asp Val Pro Phe Phe Glu Gly Leu Glu Gly Ser Ile Asp Thr Gly
145                 150                 155                 160
Ile Thr Val Ser Arg Glu Lys Val Thr Glu Val Ala Leu Lys Gly Glu
                165                 170                 175
Gly Thr Glu Glu Ala Glu Cys Lys Lys Asp Asp Ala Leu Glu Leu Gln
                180                 185                 190
Ser His Ala Lys Ser Pro Pro Ser Pro Val Glu Arg Glu Met Val Val
            195                 200                 205
Gln Val Glu Arg Glu Lys Thr Glu Ala Glu Pro Thr His Val Asn Glu
    210                 215                 220
Glu Lys Leu Glu His Glu Thr Ala Val Thr Val Ser Glu Glu Val Ser
225                 230                 235                 240
Lys Gln Leu Leu Gln Thr Val Asn Val Pro Ile Ile Asp Gly Ala Lys
                245                 250                 255
Glu Val Ser Ser Leu Glu Gly Ser Pro Pro Cys Leu Gly Gln Glu
                260                 265                 270
Glu Ala Val Cys Thr Lys Ile Gln Val Gln Ser Ser Glu Ala Ser Phe
                275                 280                 285
Thr Leu Thr Ala Ala Ala Glu Glu Lys Val Leu Gly Glu Thr Ala
    290                 295                 300
Asn Ile Leu Glu Thr Gly Glu Thr Leu Glu Pro Ala Gly Ala His Leu
305                 310                 315                 320
Val Leu Glu Glu Lys Ser Ser Glu Lys Asn Glu Asp Phe Ala Ala His
                325                 330                 335
Pro Gly Glu Asp Ala Val Pro Thr Gly Pro Asp Cys Gln Ala Lys Ser
                340                 345                 350
Thr Pro Val Ile Val Ser Ala Thr Thr Lys Lys Gly Leu Ser Ser Asp
                355                 360                 365
Leu Glu Gly Glu Lys Thr Thr Ser Leu Lys Trp Lys Ser Asp Glu Val
    370                 375                 380
Asp Glu Gln Val Ala Cys Gln Glu Val Lys Val Ser
385                 390                 395
```

(2) INFORMATION FOR SEQ ID NO:16:

(i) SEQUENCE CHARACTERISTICS:
        (A) LENGTH: 255 amino acids
        (B) TYPE: amino acid
        (C) STRANDEDNESS: single
        (D) TOPOLOGY: linear (xi) SEQUENCE DESCRIPTION: SEQ ID NO:16:

```
Val Ala Ile Glu Asp Leu Glu Pro Glu Asn Gly Ile Leu Glu Leu Glu
1               5                   10                  15
Thr Lys Ser Ser Lys Leu Val Gln Asn Ile Ile Gln Thr Ala Val Asp
                20                  25                  30
```

```
Gln Phe Val Arg Thr Glu Glu Thr Ala Thr Glu Met Leu Thr Ser Glu
            35                  40                  45

Leu Gln Thr Gln Ala His Val Ile Lys Ala Asp Ser Gln Asp Ala Gly
 50                  55                  60

Gln Glu Thr Glu Lys Glu Gly Glu Glu Pro Gln Ala Ser Ala Gln Asp
 65                  70                  75                  80

Glu Thr Pro Ile Thr Ser Ala Lys Glu Glu Ser Glu Ser Thr Ala Val
                    85                  90                  95

Gly Gln Ala His Ser Asp Ile Ser Lys Asp Met Ser Glu Ala Ser Glu
                100                 105                 110

Lys Thr Met Thr Val Glu Val Glu Gly Ser Thr Val Asn Asp Gln Gln
            115                 120                 125

Leu Glu Glu Val Val Leu Pro Ser Glu Glu Glu Gly Gly Ala Gly
130                 135                 140

Thr Lys Ser Val Pro Glu Asp Asp Gly His Ala Leu Leu Ala Glu Arg
145                 150                 155                 160

Ile Glu Lys Ser Leu Val Glu Pro Lys Glu Asp Glu Lys Gly Asp Asp
                165                 170                 175

Val Asp Asp Pro Glu Asn Gln Asn Ser Ala Leu Ala Asp Thr Asp Ala
                180                 185                 190

Ser Gly Gly Leu Thr Lys Glu Ser Pro Asp Thr Asn Gly Pro Lys Gln
195                 200                 205

Lys Glu Lys Glu Asp Ala Gln Glu Val Glu Leu Gln Glu Gly Lys Val
210                 215                 220

His Ser Glu Ser Asp Lys Ala Ile Thr Pro Gln Ala Gln Glu Glu Leu
225                 230                 235                 240

Gln Lys Gln Glu Arg Glu Ser Ala Lys Ser Glu Leu Thr Glu Ser
                245                 250                 255

(2) INFORMATION FOR SEQ ID NO:17:

(i) SEQUENCE CHARACTERISTICS:
        (A) LENGTH: 651 amino acids
        (B) TYPE: amino acid
        (C) STRANDEDNESS: single
        (D) TOPOLOGY: linear (xi) SEQUENCE DESCRIPTION: SEQ ID NO:17:

Glu Ser Ser Glu Leu Val Thr Thr Cys Gln Ala Glu Thr Leu Ala Gly
 1               5                  10                  15

Val Lys Ser Gln Glu Met Val Met Glu Gln Ala Ile Pro Pro Asp Ser
                20                  25                  30

Val Glu Thr Pro Thr Asp Ser Glu Thr Asp Gly Ser Thr Pro Val Ala
            35                  40                  45

Asp Phe Asp Ala Pro Gly Thr Thr Gln Lys Asp Glu Ile Val Glu Ile
 50                  55                  60

His Glu Glu Asn Glu Val His Leu Val Pro Val Arg Gly Thr Glu Ala
 65                  70                  75                  80

Glu Ala Val Pro Ala Gln Lys Glu Arg Pro Pro Ala Pro Ser Ser Phe
                 85                  90                  95

Val Phe Gln Glu Glu Thr Lys Glu Gln Ser Lys Met Glu Asp Thr Leu
                100                 105                 110

Glu His Thr Asp Lys Glu Val Ser Val Glu Thr Val Ser Ile Leu Ser
            115                 120                 125

Lys Thr Glu Gly Thr Gln Glu Ala Asp Gln Tyr Ala Asp Glu Lys Thr
130                 135                 140
```

-continued

```
Lys Asp Val Pro Phe Phe Glu Gly Leu Glu Gly Ser Ile Asp Thr Gly
145                 150                 155                 160

Ile Thr Val Ser Arg Glu Lys Val Thr Glu Val Ala Leu Lys Gly Glu
            165                 170                 175

Gly Thr Glu Glu Ala Glu Cys Lys Lys Asp Asp Ala Leu Glu Leu Gln
        180                 185                 190

Ser His Ala Lys Ser Pro Pro Ser Pro Val Glu Arg Glu Met Val Val
    195                 200                 205

Gln Val Glu Arg Glu Lys Thr Glu Ala Glu Pro Thr His Val Asn Glu
210                 215                 220

Glu Lys Leu Glu His Glu Thr Ala Val Thr Val Ser Glu Glu Val Ser
225                 230                 235                 240

Lys Gln Leu Leu Gln Thr Val Asn Val Pro Ile Ile Asp Gly Ala Lys
            245                 250                 255

Glu Val Ser Ser Leu Glu Gly Ser Pro Pro Cys Leu Gly Gln Glu
        260                 265                 270

Glu Ala Val Cys Thr Lys Ile Gln Val Gln Ser Ser Glu Ala Ser Phe
        275                 280                 285

Thr Leu Thr Ala Ala Ala Glu Glu Lys Val Leu Gly Glu Thr Ala
290                 295                 300

Asn Ile Leu Glu Thr Gly Glu Thr Leu Glu Pro Ala Gly Ala His Leu
305                 310                 315                 320

Val Leu Glu Glu Lys Ser Ser Glu Lys Asn Glu Asp Phe Ala Ala His
            325                 330                 335

Pro Gly Glu Asp Ala Val Pro Thr Gly Pro Asp Cys Gln Ala Lys Ser
        340                 345                 350

Thr Pro Val Ile Val Ser Ala Thr Thr Lys Lys Gly Leu Ser Ser Asp
        355                 360                 365

Leu Glu Gly Glu Lys Thr Thr Ser Leu Lys Trp Lys Ser Asp Glu Val
        370                 375                 380

Asp Glu Gln Val Ala Cys Gln Glu Val Lys Val Ser Val Ala Ile Glu
385                 390                 395                 400

Asp Leu Glu Pro Glu Asn Gly Ile Leu Glu Leu Glu Thr Lys Ser Ser
                405                 410                 415

Lys Leu Val Gln Asn Ile Ile Gln Thr Ala Val Asp Gln Phe Val Arg
            420                 425                 430

Thr Glu Glu Thr Ala Thr Glu Met Leu Thr Ser Glu Leu Gln Thr Gln
        435                 440                 445

Ala His Val Ile Lys Ala Asp Ser Gln Asp Ala Gly Gln Glu Thr Glu
    450                 455                 460

Lys Glu Gly Glu Glu Pro Gln Ala Ser Ala Gln Asp Glu Thr Pro Ile
465                 470                 475                 480

Thr Ser Ala Lys Glu Glu Ser Glu Ser Thr Ala Val Gly Gln Ala His
                485                 490                 495

Ser Asp Ile Ser Lys Asp Met Ser Glu Ala Ser Glu Lys Thr Met Thr
            500                 505                 510

Val Glu Val Glu Gly Ser Thr Val Asn Asp Gln Gln Leu Glu Glu Val
        515                 520                 525

Val Leu Pro Ser Glu Glu Gly Gly Gly Ala Gly Thr Lys Ser Val
        530                 535                 540

Pro Glu Asp Asp Gly His Ala Leu Leu Ala Glu Arg Ile Glu Lys Ser
545                 550                 555                 560
```

-continued

```
Leu Val Glu Pro Lys Glu Asp Glu Lys Gly Asp Asp Val Asp Pro
            565                 570                 575
Glu Asn Gln Asn Ser Ala Leu Ala Asp Thr Asp Ala Ser Gly Gly Leu
            580                 585                 590
Thr Lys Glu Ser Pro Asp Thr Asn Gly Pro Lys Gln Lys Glu Lys Glu
            595                 600                 605
Asp Ala Gln Glu Val Glu Leu Gln Glu Gly Lys Val His Ser Glu Ser
    610                 615                 620
Asp Lys Ala Ile Thr Pro Gln Ala Gln Glu Glu Leu Gln Lys Gln Glu
625                 630                 635                 640
Arg Glu Ser Ala Lys Ser Glu Leu Thr Glu Ser
            645                 650
```

(2) INFORMATION FOR SEQ ID NO:18:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:18:

```
Asp Leu Ile Glu Glu Ala Ala Ser Arg Pro Val Asp Ala Val Ile
1               5                   10                  15
Glu Gln Val Lys Ala Ala Gly Ala
                20
```

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:19:

GACGAGATTG TGGAAATCCA TGAGG                                  25

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:20:

GCGCGGATCC AGAGATTCTG TAGTTCTGAC                          30

(2) INFORMATION FOR SEQ ID NO:21:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO:21:

```
Phe Lys Lys Phe Phe Thr Gln Gly Trp Ala Gly Trp Arg Lys Lys Thr
1               5                   10                  15
Ser Phe Arg Lys Pro Lys
                20
```

-continued (2) INFORMATION FOR SEQ ID NO:22:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:22:

Pro Leu Lys Lys Leu Phe Thr Ser Thr Gly Leu Lys Lys Leu Ser Gly
1          5                   10               15

Lys Lys Gln Lys Gly Lys Arg
         20

(2) INFORMATION FOR SEQ ID NO:23:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO:23:

Lys Ala Ser Met Leu Cys Phe Lys Arg Arg Lys Lys Ala Ala Lys Leu
1          5                   10               15

Ala Lys Pro Lys Ala Gly
         20

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:24:

Val Arg Lys Arg Thr Leu Arg Arg Leu
1          5

PROTEIN BINDING FRAGMENTS OF GRAVIN

This application is a continutation-in-part of co-pending U.S. patent application Ser. No. 08/769,309 filed on Dec. 19, 1996 now U.S. Pat. No. 5,741,890.

FIELD OF THE INVENTION

The present invention relates generally to proteins that maintain the subcellular localization of kinases. More specifically, this invention relates to polypeptide fragments of a protein, gravin, which binds to a regulatory subunit of cAMP-dependent protein kinase or to protein kinase C. The invention also relates to methods of modulating the interaction of gravin and its binding partners.

BACKGROUND OF THE INVENTION

Protein kinases are ubiquitous enzymes expressed in all eukaryotic cells and are involved in cellular responses to physiological stimuli. Protein kinases attach phosphate groups to substrate proteins. Cyclic-AMP (cAMP) dependent protein kinase (PKA) is an enzyme with broad substrate specificity which phosphorylates substrate proteins in response to cAMP. Protein kinase C (PKC) is an enzyme which phosphorylates substrate proteins in response to intracellular $Ca^{2+}$ and phospholipid.

Many hormones act through common signal transduction pathways that generate the intracellular second messenger cAMP. The predominant action of cAMP is to activate a PKA by binding to the regulatory subunit (R) dimer of the holoenzyine thereby releasing the catalytic (C) subunit. Free C subunit potentiates hormonal responses by phosphorylating substrate proteins near the site of kinase activation.

Two classes of the R subunit have been identified; RI and RII subunits which respectively form the type I and type II PKA holoenzymes. The subcellular distributions of PKA isoforms appear to be distinct. The RI isoforms (RIα and RIβ) are reported to be predominantly cytoplasmic and are excluded from the nuclear compartment, whereas up to 75% of the RII isoforms (RIIα or RIIβ) are particulate and associate with the plasma membrane, cytoskeletal components, secretory granules, the golgi apparatus, centrosomes and/or possibly nuclei. (RIIα or RIIβ) are particulate and associate with the plasma membrane, cytoskeletal components, secretory granules, the golgi apparatus, centrosomes and/or possibly nuclei.

Intracellular transduction of signals from the plasma membrane to specific subcellular compartments is a complex and highly regulated series of events which control essential physiological processes. An example of signaling pathway involvment are essential in maintaining cellular homeostasis appears in Hunter, *Cell*, 80:225–236 (1995) where it was shown that many transforming oncogenes encode signal transduction components such as low molecular weight G proteins, protein kinases, or phosphatases. Phosphatases remove phosphate groups from proteins or other compounds. Kinase and phosphatase activities thus control intracellular signal transduction by phosphorylating and dephosphorylating substrate molecules. Now that many genes encoding these proteins have been identified, research emphasis has begun to focus on how these enzymes interface to control cellular events. A critical element in this operation is the subcellular location of each signaling enzyme. For example, Newton, *Current Biology*, 6:806–809 (1996) showed that the correct intracellular targeting of kinases and phosphatases directs these enzymes to their preferred substrates and reduces indiscriminate background phosphorylation and dephosphorylation.

Kinase and phosphatase targeting is achieved through association with targeting proteins or subunits [reviewed by Faux and Scott, *TIBS*, 21:312–315 (1996b)]. For example, tyrosine kinase (PTK) and tyrosine phosphatase (PTPase) activity are coupled to downstream cytoplasmic enzymes through adaptor proteins that contain SH2 and SH3 domains. SH2 domains recognize certain phosphotyrosyl residues and SH3 domains bind to a PXXP motif found in some kinases and phosphatases. Modular adaptor proteins like Grb2, p85, IRS-1, Crk and Nck comprise a single SH2 domain that recognizes phosphotyrosyl residues of signalling enzymes and two SH3 domains that bind to the PXXP motif on a separate set of target proteins. Similarly, many phospholipases, kinases, phosphatases and heterotrimeric G-proteins are targeted by specific membrane-targeting motifs such as the LIM, C2, pleckstrin homology and lipid anchoring domains [Gill, *Structure*, 3:1285–1289 (1995); Newton, *Current Biology*, 5:973–976 (1995)]. Through these interactions, signaling complexes assemble around receptor kinases or scaffold proteins to mediate cellular processes including hormone signaling events and immune cell function [Harrison et al., *TIBS*, 20:1213–1221 (1995)].

Until recently, second messenger-stimulated kinases and phosphatases were thought to be localized through association with individual targeting proteins. For example, three classes of phosphatase targeting subunits have been identified which are specific for protein phosphatase I [Chen et al. *FEBS Letters*, 356:51–55 (1994)]; protein phosphatase 2A [Csortos et al., *J. Biol. Chem.*, 271:2578–2588 (1996)]; or protein phosphatase 2B [Shibasaki et al., *Nature*, 382:370–373 (1996)]. Likewise, three classes of PKC targeting proteins have been identified in Chapline et al., *J. Biol. Chem.* 268:6858–6861 (1993); Mochly-Rosen, 1995; and Staudinger et al., *J. Cell Biol.*, 128:263–271 (1995). Compartmentalization of PKA is achieved through interaction of the R subunits with a functionally related family of thirty or so A-Kinase Anchoring Proteins, called AKAPs [reviewed in Scott and McCartney, *Molecular Endocrinology*, 8:5-13 (1994)]. The present invention contemplates that anchoring proteins confer specificity on serine/threonine kinases and phosphatases by directing these enzymes to discrete subcellular sites where they have restricted access to certain substrates and are optimally positioned to respond to fluctuations in the levels of second messengers.

A variation on this theme was reported in the recent identification of multivalent binding proteins that coordinate the location of serine/threonine kinase and phosphatase signaling complexes. For example, Herskowitz, *Cell*, 80:187–197 (1995) showed that the pheromone mating response in yeast is initiated through a G-protein linked receptor that activates a yeast MAP kinase cascade. This process proceeds efficiently because each enzyme in the cascade is associated with a scaffold protein called sterile 5 (STE 5) [Choi et al., *Cell*, 78:499–512, (1994)]. Clustering of successive members in the MAP kinase cascade allows for the tight regulation of the pathway and prevents "crosstalk" between the six functionally distinct MAP kinase modules in yeast [Herskowitz et al., 1995]. Another example of a multivalent binding protein is AKAP79 which targets PKA, PKC and protein phosphatase 2B at the postsynaptic densities of mammalian synapses [Klauck et al., *Science*, 271:1589–1592 (1996); Coghlan, et al., (1995b). The structure of AKAP79 is modular and resembles STE 5. Deletion analysis, peptide studies and co-precipitation studies of AKAP79 and STE5 have demonstrated that enzymes bind to distinct regions of the anchoring protein [Klauck et al., 1996]. Targeting of the AKAP79 signaling complex to the postsynaptic densities suggests a model for reversible phosphorylation in which the opposing effects of kinase and phosphatase action are co-localized by a common anchoring protein [Coghlan et al., *Advances in Protein Phosphatases*, 6:51–61 (1995a)].

AKAPs have been identified in a variety of organisms. At least seven proteins that bind the regulatory subunit of PKA in *Aplysia californica*, a marine invertebrate, have been identified [Cheley et al., *J. Biol. Chem.*, 269:2911–2920 (1994)]. One of these proteins is enriched in crude membrane fractions and taxol-stabilized microtubules and may thus anchor microtubules to the cell membrane as well as bind PKA. A mammalian AKAP microtubule-associated protein 2 (MAP2) attaches PKA to the cytoskeleton [DeCamilli et al., *J. Cell Biol.*, 103:189–203 (1986)]. The PKA-binding site on MAP2 is a 31-residue peptide in the amino-terminal region of the MAP2 molecule [Rubino et al., *Neuron*, 3:631–638 (1989)].

To date, a number of AKAPs have been identified which apparently bind PKA by a common secondary structure motif that includes an amphipathic helix region [Scott and McCartney, 1994]. Binding of PKA to most, if not all, identified AKAPs can be blocked in the presence of a peptide (Ht31) (SEQ ID NO: 8) that mimics the common secondary structure, while a mutant Ht31peptide containing a single amino acid substitution (SEQ ID NO: 18) that disrupts the secondary structure of the peptide has no effect on PKA/AKAP binding [Carr et al, *J. Biol. Chem.*, 266:14188–14192 (1991)]. Even though PKA/AKAP interaction is effected by a common secondary structure, AKAPs (or homologous AKAPs found in different species) generally have unique primary structure as is evidenced by the growing number of AKAPs that have been identified in a variety of organisms. The unique structure in each anchoring protein confers specificity on a kinase by targeting an AKAP signalling complex to specific intracellular locations.

Chapline and co-workers recently reported the cloning of a PKC binding protein identified as "clone 72" [Chapline et al., *J. Biol. Chem.*, 271:6417–6422 (1996)]. Interestingly, Clone 72 was shown to have substantial homology to a mitogenic regulatory gene identified as "clone 322" [Lin et al., *Mol. Cell. Biol.*, 15:2754–2762 (1995)]. Clone 322 was identified as being the same molecule identified as "SSeCKS" in Lin, et al., *J. Biol. Chem.* 271:28340–28348 (1996). Clone 322 was shown to be down-regulated in oncogene (e.g., src, ras, fos and myc) transformed cells and thus appears to be a tumor suppressor gene.

Also of interest to the invention is *Myasthenia gravis* (MG), a disease of neuromuscular transmission characterized by weakness and rapid fatigability of the muscles. It is believed that MG is an autoimmune disease in which the patient develops antibodies to the nicotinic acetylcholine receptor. The nicotinic acetylcholine receptor controls a cation channel in response to binding of acetylcholine. In addition, development of autoantibodies to other cytoskeletal antigens including alpha actinin, actin, filamin and vinculin is observed in the MG patient. The muscle weakness appears to be caused by a failure of the nicotinic acetylcholine receptor as the autoantibodies apparently participate in destruction of the nicotinic acetylcholine receptors.

A previously unknown MG antigen, gravin, was identified by expression screening of a cDNA library with serum from a patient suffering from MG [Gordon et al., *J. Clin. Invest.*, 90:992–999 (1992)]. Gordon, et al. disclosed amino acid sequences disclosing 306 C-terminal amino acid residues of gravin and the corresponding polynucleotide. Gravin was shown to be expressed on the cell cortex and was also shown to be expressed in migratory cells such as fibroblasts and neurons, but not in stationary cells such as epithelial cells. In addition, gravin was found to be expressed in adherent cells, but not in non-adherent cells. Therefore, gravin was postulated to play a role in cell migration and/or cellular adhesion [Grove et al., *Anat. Rec.*, 239:231–242 (1994)].

There continues to exist a need in the art for further insights into the nature, function,and distribution of anchoring proteins and the role of anchoring proteins in myasthenia gravis.

SUMMARY OF THE INVENTION

This present invention is based on the discovery that gravin is a kinase anchoring protein that binds to the type II regulatory subunits of PKA and to PKC. The complete amino acid sequence of gravin is provided herein. In binding to protein kinases, gravin localizes kinases to a specific subcellular region(s) and may regulate the function of the kinases and thereby control cellular signalling.

In one aspect, the present invention provides a gravin polypeptide fragment that binds to the type II regulatory subunit of PKA. Preferably, the polypeptide fragment comprises amino acid residues 1526–1582 (SEQ ID NO: 1) of gravin. More preferably, the polypeptide fragment comprises amino acid residues 1537–1563 (SEQ ID NO: 2) of gravin.

In another aspect, the present invention provides a polypeptide fragment that binds to PKC. Preferably, the polypeptide fragment comprises amino acid residues 265–556 (SEQ ID NO: 3) of gravin.

Yet another aspect of this invention provides polypeptide analogs of such fragments. Analogs are fragments in which additions, substitutions, including conservative substitutions, or deletions of amino acid residues have been made in order to increase or decrease the binding affinity of the analog fragment for a protein kinase. These analogs of gravin may be useful for modulating (i.e., blocking, inhibiting, or stimulating) the interaction between gravin and the kinase.

The polypeptides of the present invention are synthesized in solution or on a solid support in accordance with conventional techniques as described in Stewart and Young, *Solid Phase Peptide Synthesis*, 2nd ed., Pierce Chemical Company, (1984) or Tam et at., *J. Am. Chem. Soc.*, 105:6442 (1983), both of which are incorporated herein by reference.

The polypeptides of this invention may be modified to facilitate passage into the cell, such as by conjugation to a lipid soluble moiety. For example, the peptides may be conjugated to myristic acid. The peptides may be myristoylated by standard techniques as described in Eichholtz et at., *J. Biol. Chem.* 268:1982–1986 (1993), incorporated herein by reference. Alternatively, the peptides may be packaged in liposomes that may fuse with cell membranes and deliver the peptides into the cells. Encapsulation of the peptides in liposomes may also be performed by standard techniques as generally described in U.S. Pat. Nos. 4,766,046; 5,169,637; 5,180,713; 5,185,154; 5,204,112; and 5,252,263 and PCT Patent Application No. 92/02244, each of which is incorporated herein by reference.

Another aspect of the invention provides polynucleotides encoding the protein binding fragments of gravin. Polynucleotides of the invention include DNA (i.e., genomic, complementary, and synthetic) and RNA. Sense and antisense polynucleotides, complementary to coding and non-coding polynucleotides are also contemplated. The polynucleotides of the present invention can be generated and purified by any number of standard, well-known techniques in the art. Also contemplated are polynucleotides which code for the polypeptides of the present invention based upon degeneracy of the genetic code. In addition, polynucleotides which encode gravin (e.g., degenerate oligoiners) useful in polymerase chain reaction (PCR) technologies are contemplated. Polynucleotides encoding analogs of gravin or structurally related DNAs which hybridize under stringent hybridization conditions to the polynucleotides of the invention are also contemplated. Those of ordinary skill in the art will understand hybridization conditions described as "stringent."

Exemplary stringent hybridization conditions are as follows: hybridization at about 65° C. in 3×SSC, 20 mM $NaPO_4$ pH 6.8 and washing at about 65° C. in 0.2×SSC. It is understood by those of skill in the art that variation in these conditions occurs based on the length and GC nucleotide base content of the sequences to be hybridized. Formulas standard in the art are appropriate for determining exact hybridization conditions. See Sambrook et al., 9.47–9.51 in *Molecular Cloning*, Cold Spring Harbor Laboratory Press, Cold Spring Harbor, N.Y. (1989).

Polynucleotides of the invention are useful for recombinant production of the kinase binding domain polypeptides. Vectors comprising polynucleotides encoding a kinase binding domain as well as promotor, selectable marker and other well-known vector components (e.g. origin of replication, multiple cloning sites, etc.) are also contemplated by the invention.

The skilled artisan will understand the various components of vectors, methods for manipulating and the uses of vectors in transforming or transfecting of host cells (prokaryotic and eukaryotic) and expressing the kinase binding domains of the present invention. Host cells, especially unicellular host cells such as procaryotic and eukaryotic cells, are stably or transiently transformed or transfected with DNAs of the invention in a manner allowing expression of the kinase binding fragments of gravin. Host cells of the invention are conspicuously useful in methods for the large scale production of protein binding fragments of gravin wherein the cells are grown in a suitable culture medium and the desired fragments are isolated from the cells or from the medium in which the cells are grown. Use of mammalian host cells is expected to provide for such post-translational modifications (e.g., myristoylation, glycosylation, proteolytic processing, lipidation and tyrosine, serine or threonine phosphorylation) as may be needed to confer biological activity on recombinant expression products of the invention.

Another aspect of this invention provides antibody substances (e.g., polyclonal and monoclonal antibodies, antibody fragments, single chain antibodies, chinmeric antibodies, CDR-grafted antibodies, humanized antibodies and the like) specifically immunoreactive with the protein binding domains of gravin. Antibody substances can be prepared by standard techniques using isolated naturally-occurring or recombinant gravin. The antibody substances are useful in modulating (i.e., blocking, inhibiting, or stimulating) the binding between gravin and the kinase and in detecting gravin in patients suffering from MG. In addition, cell lines, (e.g., hybridomas), or cell lines transformed with recombinant expression constructs which produce antibody substances of the invention are contemplated.

In another aspect, methods of identifying a modulator compound that inhibits or increases binding between a gravin polypeptide and a gravin binding partner (e.g., type II regulatory subunit of PKA or PKC) are contemplated. In one method, gravin or a polypeptide fragment thereof such as set out in SEQ ID NOs: 1, 2 or 3 and a binding partner are incubated in the presence and absence of a putative modulator compound under conditions suitable for binding. The amount of binding in the presence and in the absence of the putative test compound is determined and compared. A reduction in the amount of binding observed in the presence of the test compound indicates that the test compound is an inhibitor. An increase in the amount of binding observed in the presence of the test compound indicates that the test compound increases binding between gravin and the binding partner. In one embodiment, either gravin or the binding partner can be immobilized on a solid substrate, and either gravin or the binding partner is detectably labeled. In addition, other assays, such as scintillation proximity assays may also be employed.

Modulators are useful for example, in inhibiting localization of a gravin binding partner (e.g. PKA, PKC, or other kinases) to a specific subcellular location. The contemplated modulators include polypeptides, polypeptide fragments of gravin and other organic and inorganic compounds.

The DNA sequence information provided by the present invention also makes possible the development, by homologous recombination or "knockout" strategies [see e.g. Capecchi, *Science* 244:1288–1292 (1989)] of mammals that fail to express functional gravin or that express an analog of gravin. The mammals of the present invention comprise a disruption of the gravin gene of the mammal or the disruption of a homolog of the gravin gene. The general strategy utilized to produce the mammals of the present invention involves the preparation of a targeting construct comprising DNA sequences homologous to the endogenous gene to be disrupted. The targeting construct is then introduced into embryonic stem cells (ES cells) whereby it integrates into and disrupts the endogenous gene or homolog thereof. After selecting cells which include the desired disruption, the selected ES cells are implanted into an embryo at the blastocyst stage. Exemplary mammals include rodent species.

Numerous additional aspects and advantages of the present invention will be apparent from the following detailed description of illustrative embodiments thereof.

DETAILED DESCRIPTION OF THE INVENTION

Figure 1A:
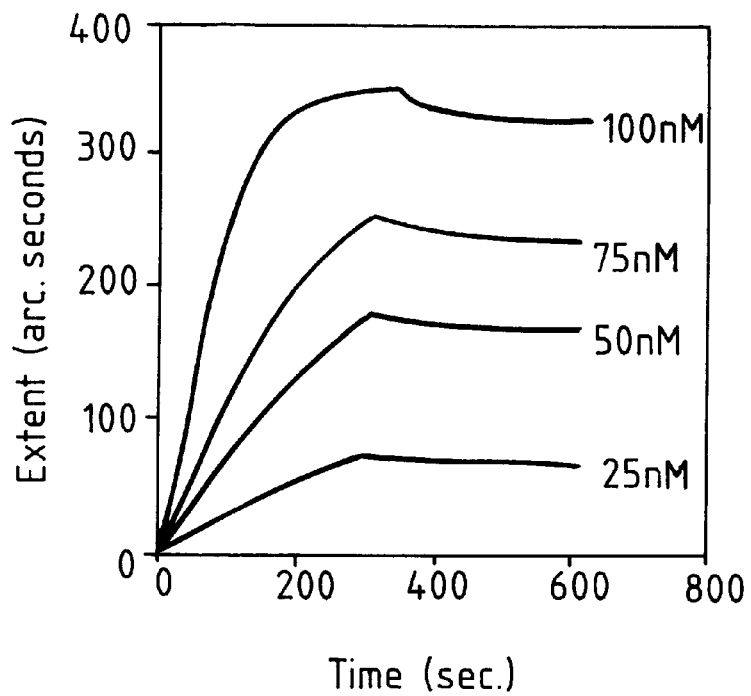
FIG. 1A. Binding properties of immobilized gravin fragment measured over a range of R11α 1–45 concentrations from 25–150 nM.

The present invention is illustrated by the following examples. Example 1 describes the cloning and characterization of a cDNA encoding gravin. The mapping and identification of a fragment of gravin that binds to the type II regulatory subunit of PKA is disclosed in Example 2. Example 3 describes the expression of full length gravin in COS cells. Example 4 describes the mapping and identification of a PKC binding fragment of gravin. Example 5 discusses the preparation of monoclonal and polyclonal antibodies. Experiments describing gravin expression in human erythroleukemia cells (HEL) is provided in Example 6. Example 7 describes experiments identifying tissue distribution of gravin. Example 8 describes the role of gravin in signal transduction and Example 9 describes binding assays utilizing gravin an a binding partner. Example 10 describes gravin's role in cell adhesion. In light of the present disclosure, those of skill in the art will appreciate that the following examples are intended to be illustrative only and that numerous changes, modifications and alterations can be made without departing from the spirit and scope of the invention.

EXAMPLE 1

To isolate cDNAs encoding potential RII binding proteins, a human fetal brain λ-ZAP cDNA library was screened by a modified overlay procedure using radiolabeled RIIα as a probe [Lohmann et al., *Proc. Natl. Acad. Sci. U.S.A.*, 81:6723–6727 (1984)]. Eight RII binding clones were identified, plaque purified and the ends of each insert were sequenced. Two of the clones represented known sequences. One matched MAP2, a previously identified AKAP [Theurkauf et al., *J. Biol. Chem.*, 257:3284–3290 (1982)]. The 3' end of another clone, designated HF 9, was identical to a previously described partial clone encoding gravin, which was originally isolated by screening a Human Umbilical Vein Endothelial cell (HUVE) cDNA library with serum from a *Myasthenia gravis* patient [Gordon et al., 1992].

Further sequencing of clone HF 9 showed that the cDNA insert was 3023 base pairs in length and encoded a continuous open reading frame of 651 amino acids. Northern blot analysis using a $^{32}$p random primed 1676 base pair Eco RI-Spe I fragment of HF 9 as a probe indicated that gravin mRNA was selectively expressed in certain human tissues. Two predominant mRNA species of 8.4 kb and 6.7 kb were detected in all tissues but predominated in liver, brain and lung, whereas an additional 5.5 kb message was detected in brain. The larger sizes of all the gravin messages, indicated that the HF 9 clone represented a partial cDNA. Therefore, the 1676 base pair HF 9 fragment was used to further screen the human fetal brain cDNA library for more complete transcripts. Five additional clones were obtained that yielded an additional 600 base pairs of coding region. As an alternative strategy, a human heart cDNA library was screened with the same 1676 base pair HF 9 fragment. Of the five positive clones isolated from the heart cDNA library, the longest clone contained a 4216 base pair insert, which overlapped with the 5' end of HF 9. This provided a contiguous composite sequence of 6605 base pairs encoding a protein of 1780 amino acids. The complete DNA and amino acid sequences of this protein, human gravin, are presented in SEQ ID NO: 4 and 5, respectively.

EXAMPLE 2

The last 651 amino acids of gravin were demonstrated to contain a binding site for association with the type II regulatory subunit of PKA. It was previously shown that regions of conserved secondary structure which are likely to include amphipathic u-helices are responsible for RII-binding [Carr et al., *J. Biol. Chem.*, 267:13376–13382 (1992)]. Residues 1540–1553 LETKSSKLVQNIIQ (SEQ ID NO: 6) of gravin fulfilled these criteria. These residues also show sequence identity with corresponding regions in other AKAPs and a helical-wheel plot suggested that there was a segregation of hydrophobic and hydrophilic side-chains which is compatible with the formation of an amphipathic helix. The RIIα binding fragment of gravin also shows some sequence homology to the corresponding RII binding regions in AKAP79 (LIETASSLVKNAIQ) (SEQ ID NO: 7) and in Ht31 (DLIEEAASRIVDAVIEQVKAAGA) (SEQ ID NO: 8). Ht31 is a sequence derived from human thyroid AKAP.

To identify the RII binding site(s) of gravin, a family of recombinant DNAs encoding fragments of gravin were generated by PCR using HF9 as the template. The polynucleotides encoding these fragments were subcloned into the pET16d plasmid which provides nucleotide sequences encoding a histine tag expressed at the amino terminus of the expressed gravin fragment. These constructs were expressed in *E. coli* and purified using the pET16d Histag bacterial expression/affinity purification system. Constructs encoding putative RII-binding site residues 1130–1582 (SEQ ID NO: 17) and 1130–1525 (SEQ ID NO: 15) of gravin were generated by utilizing a common 5' primer, CCGCCATGGTGCATATGTCCGAGTCCAGTGAGC, (SEQ ID NO: 9) but utilized distinct 3' primers: GCGCG-GATCCGCACTCACTTTGACCTCCTG (SEQ ID NO: 10) for residues 1130–1525 (SEQ ID NO: 15) and GCGCG-GATCCGCTATCACGTGAGCTTGTGT (SEQ ID NO: 11) for residues 1130–1582 (SEQ ID NO: 14). The 1526–1780 (SEQ ID NO: 16) construct was prepared by using the 5' primer, CCGCCATGGTGCATATGGTAGCAAT-TGAGGATTTAG (SEQ ID NO: 12) in conjunction with the 3' primer, GGAGGATCCAGAGATTCTGTAGTTCTG (SEQ ID NO: 13) used to subclone the full length clone. Each gravin construct was transfected into *E. coli* and expression of recombinant Histag fusion proteins was induced by IPTG. Each recombinant protein was purified according to previously published methods [Coghlan et al., *Science*, 267:108–111 (1995b)].

The gravin fragments were screened for RIIα binding using an overlay procedure essentially as described in Lohman et al., *Proc. Nat. Acad. Sci.*, 81:6723–6727 (1984). Briefly, the overlay procedure is performed as follows. Protein samples are separated by SDS polyacrylamide gel electrophoresis (PAGE) and transferred to nitrocellulose by standard electrotransfer techniques. The immobilized protein is partially renatured by incubation in a blocking solution containing milk proteins then probed with $^{32}$p-labelled RII probe. After removal of unbound probe by washing, binding between gravin polypeptide fragments and RII is detected by autoradiography. To increase sensitivity of the assay (up to ten-fold), bound RII is detected immunologically (e.g. anti-RII-antisera and $^{125}$I-protein A, or monoclonal antibodies which specifically recognize RII.)

The 452 residue fragment encompassing residues 1130–1582 (SEQ ID NO: 14) bound $^{32}$P-radiolabeled RIIα in the overlay, whereas a smaller fragment, residues 1130–1525 (SEQ ID NO: 15), which lacked the RII-binding region was unable to bind RIIα.

Two additional experiments provided evidence that the putative amphipathic helix region was sufficient for RII-binding. The fragment encompassing residues 1526–1780 (SEQ ID NO: 16) of gravin bound RII in the overlay and a synthetic peptide covering residues 1537–1563 (SEQ ID NO: 2) blocked all RII-binding in the overlay. In addition, the anchoring protein inhibitor peptide Ht31 (DLIEEAASRIVDAVIEQVKAAGA) (SEQ ID NO: 8) which is a competitive inhibitor of RII/AKAP interactions also blocked RII binding to gravin as assessed by the overlay assay. Control experiments in which overlays were performed in the presence of 0.3 µM inhibitor polypeptide Ht31 (SEQ ID NO: 8) confirmed that the Ht31 inhibited binding between gravin and RIIα. In addition a second control peptide, Ht31-pro, (DLIEEAASRPVDAVIEQVKAAGA) (SEQ ID NO: 18) which is unable to block RII/AKAP binding was unable to inhibit binding between gravin and RIIα. The second control peptide (SEQ ID NO: 18) is the Ht31 peptide in which an isoleucine has been replaced by a proline thereby disrupting the secondary structure. The Ht31 (SEQ ID NO: 8) peptide and Ht31-pro peptide were synthesized. To facilitate labeling and/or tracking of the control peptides, an additional tyrosine (radioiodination) or lysine (biotin/avidin) residue was sometimes included at the C-tenninus of the control peptides. This data demonstrates that gravin is an AKAP and its principle RII-binding site is encompassed by residues 1526–1582 (SEQ ID NO: 1).

Figure 1B:
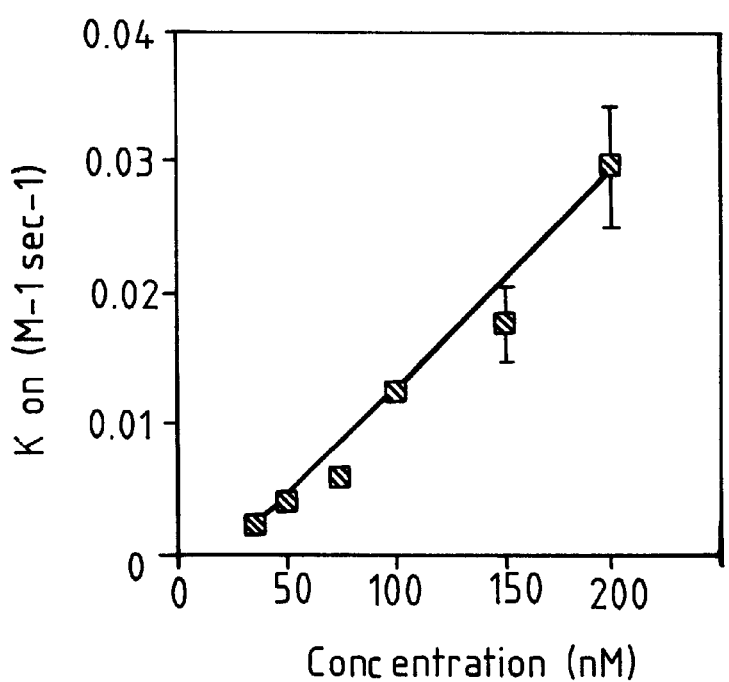
FIG. 1B. Uniform first order binding of immobilized gravin fragment.

This finding was further confinned when the binding affinity of the gravin 1526–1780 (SEQ ID NO: 16) fragment for a recombinant fragment of RIIα was measured by surface plasmon resonance (SPR). SPR is an analytical technique that utilizes evanescent light to examine macromolecular complexes. The binding affinities of one protein to an immobilized binding partner can be measured by SPR. A recombinant fragment encompassing residues 1526–1780 (SEQ ID NO: 16) of gravin was coupled to a carboxymethyldextran IAsys cuvette using standard EDC/NHS coupling chemistry [Davies et al., *Techniques in Protein Chemistry*, 5:285–2992 (1994)]. The cuvette was activated by treating with 0.4 M EDC/0.1 M NHS for 8 min and washed extensively with PBST (PBS+0.05% Tween-20). Coupling of the gravin 1526–1780 fragment (SEQ ID NO: 16) (25 µg/ml) was accomplished in 10 mM formate buffer, pH 3.6 for 10 min at room temperature. Uncoupled protein was washed out with PBST and free amines were blocked with 1M ethanolamine, pH 8.5 for 2 min at room temperature. After washing with PBST, a stable baseline was established for 10 min before data collection. All binding experiments were performed with a recombinant fragment of RIIα (RII 1–45) [Scott, et al., *Pro. Nat. Acad. Sci.* 84:5192–5196 (1987)] which binds AKAPs with a similar affinity as the full-length protein. Previous experiments have indicated that release of RIIα 1–45 from the binding surface can be performed under conditions that are less harmful to the immobilized anchoring protein than studies using full length RII. Binding experiments were performed over a range of concentrations from 25 to 150 nM in volumes of 200 µl. The binding surface was regenerated between binding measurements using 60% ethanol with no decrease in extent measurements over the duration of an experiment. Data collection was done over three second intervals and was analyzed using the Fastfit™ software which was provided with the IAsys instrument. The binding properties of the immobilized gravin fragment were measured over a range of RIIα 1–45 concentrations from 25 to 150 nM (FIG. 1A). Uniform first order binding was recorded with a $K_{assc}$ of 160006±9700 $M^{-1}$ $sec^{-1}$ (n=3) and with a $K_{dis}$, of 0.016±0.001 $M^{-1}$ (n=3) (FIG. 1B). These values were used to calculate a dissociation constant (KD) of 100 nM (n=3) for the RII/gravin fragment interaction (FIG. 1B). The nanomolar binding constant for RII/gravin interaction is well within the physiological concentration range of both proteins inside cells and is consistent with the notion that both proteins may associate in situ.

As demonstrated above, residues fragment 1537–1563 (SEQ ID NO: 2) of gravin form a PKA anchoring site. Of note, this sequence is present in the C-terminus of SSeCKS/ clone 72 (see Example 4). Interestingly, this shared sequence has ten out of fourteen residues which are conserved in the RII-binding region of another mammalian scaffold protein, called AKAP79, which binds PKA, PKC and protein phosphatase 2B [Coghlan et al., 1995b; Klauck et al., 1996]. The identification of a conserved RII-binding sequence in gravin, SSeCKS/clone 72 and AKAP79 is the first example of conserved primary structure in known RII binding regions. This finding was unexpected as it was previously proposed that in spite of a lack of sequence identity among the AKAPs there existed a conservation of secondary structure in the RII-binding motif [Scott et al., 1994]. Therefore, it is likely that gravin, SSeCKS/clone 72 and AKAP 79 are members of a structurally related subfamily of AKAPs which bind more than one kinase or phosphatase.

EXAMPLE 3

In order to study the role of anchoring of PKA by gravin, full length gravin was expressed in cells that normally do not express the protein.

A plasmid containing the fill length gravin cDNA was prepared as follows. A 1.7 kb XbaI fragment was isolated from HF9 (containing the C-terminal sequece of Gravin) and cloned into pBSII (Strategene) containing the N-terminal 4216 bp clone (see Example 1) which was predigested with XbaI. Clones were screened and sequenced (on the 5' and 3' junctions) for correct orientation. The resulting clone is referred to as pBS/gravin. A EcoRI-Not1 fragment of pBS/Gravin was inserted in pcDNA3 predigested with EcoRI and Not1. Clones were screened for inserts by restriction digests using EcoRI and NotI. Correct clones were confirmed by sequencing the 5' and 3' junctions with primers DCO3 and JHSP6 respectively.

Transfection of Recombinant Gravin

COS cells were grown in 100 mm culture dishes until 20–40% confluent. Transfection of COS cells was performed as follows. The pcDNA3-gravin vector at a concentration of 10 µg in 150 µl serum free culture media was prepared to which was added 20 µl of SuperFect (Qiagen, Chatsworth, Calif.). Media was removed from the COS cell culture and the cells washed with CMF-PBS. The SuperFect mixture was added to 3 ml of media with 10% FBS and added to the cells for three hours at 37° C. Cells were then washed and fresh media added for an overnight incubation. Next, the cells were washed, trypsin harvested, washed again then lysed as described in Example 5. Transfection procedure for Jurkat cells was similar except the SuperFect mixture was added to Jurkat cells and left in the culture overnight. Cell lysates were prepared as described at 24, 48 hours and two weeks after transfection. Gravin expression was determined by Western blot analysis.

Transfected COS cells showed an enhanced gravin signal over baseline expression levels at twenty-four hours post transfection. Jurkat cells, which do not express gravin, showed significant expression of the recombinant protein from twenty-four hours post transfection out to two weeks. Recombinant gravin can thus be expressed and maintained in human cell lines.

EXAMPLE 4

Further sequence analysis revealed another potential function of gravin. A search of the nucleotide database using the complete gravin sequence showed that the first 1000 residues are 69% identical to a murine mitogenic regulatory protein SSeCKS [Lin et al., 1995]) also identified in the art as "clone 72", which was recently shown to be a protein kinase C binding-protein and also a protein kinase C substrate. [Chapline et al., 1996].

The ability of gravin to bind PKC was therefore examined. Accordingly, two recombinant gravin polypeptide fragments consisting of amino acids 265–556 (SEQ ID NO: 3) and 1130–1582 (SEQ ID NO: 14) were prepared and overlay analysis similar to the overlay analysis described in Example 2 was performed. The immobilized gravin fragments were incubated with PKC and the bound PKC was detected by using monoclonal antibodies to PKC (Transduction Labs, Lexington, Ky.) [Klauck, et al., (1996)]. The 265–556 (SEQ ID NO: 3) fragment was prepared by PCR using primers GACGAGATTGTGGAAATCCATGAGG (SEQ ID NO: 19) and GCGCGGATCCAGAGATFCTGTAGRFCTGAC (SEQ ID NO: 20). The 1130–1582 (SEQ ID NO: 14) fragment was prepared as described in Example 2. The results showed that PKC bound to the 265–556 fragment (SEQ ID NO: 3), but not to the 1130–1582 fragment (SEQ ID NO: 14). The overlay assay thus showed that the PKC binding fragment of gravin mapped to a region of the sequence between residues 265 to 556 (SEQ ID NO: 3). Neither of the gravin fragments bound PKC in the absence of phosphatidylserine (PS) which is consistent with other reports that phospholipid is a co-factor in the PKC/binding protein complex [Chapline et al., 1996]. It has been suggested that phosphatidylserine (PS) supports a ternary complex of PKC and polybasic regions on the substrate/binding protein [Liao et al., *Biochem.*, 33:1229–1233 (1994)].

Polybasic regions were postulated to participate in formation of a phospholipid bridge between the PKC and its binding proteins [Chapline et al., 1996; Chapline et al., 1993]. In AKAP79, a polybasic region was identified as the PKC binding site [Klauck et al., 1996]. In gravin, there are two polybasic regions in the gravin 265–556 fragment (SEQ ID NO: 3) located between residues 295–316 (FKKFFTQGWAGWRKKTSFRKPK) (SEQ ID NO: 23) and 514–536 (PLKKLFTSTGLKKLSGKKQKGKR) (SEQ ID NO: 24). Both polybasic regions (residues 295–316 and residues 514–536) resemble the PKC-binding site on AKAP79. Synthetic peptides of both polybasic regions of gravin blocked PKC/gravin interactions when assessed by the overlay assay. These experiments show that protein kinase C binds gravin in vitro at one or more polybasic sites located between residues 265–556 of the protein.

Figure 2:
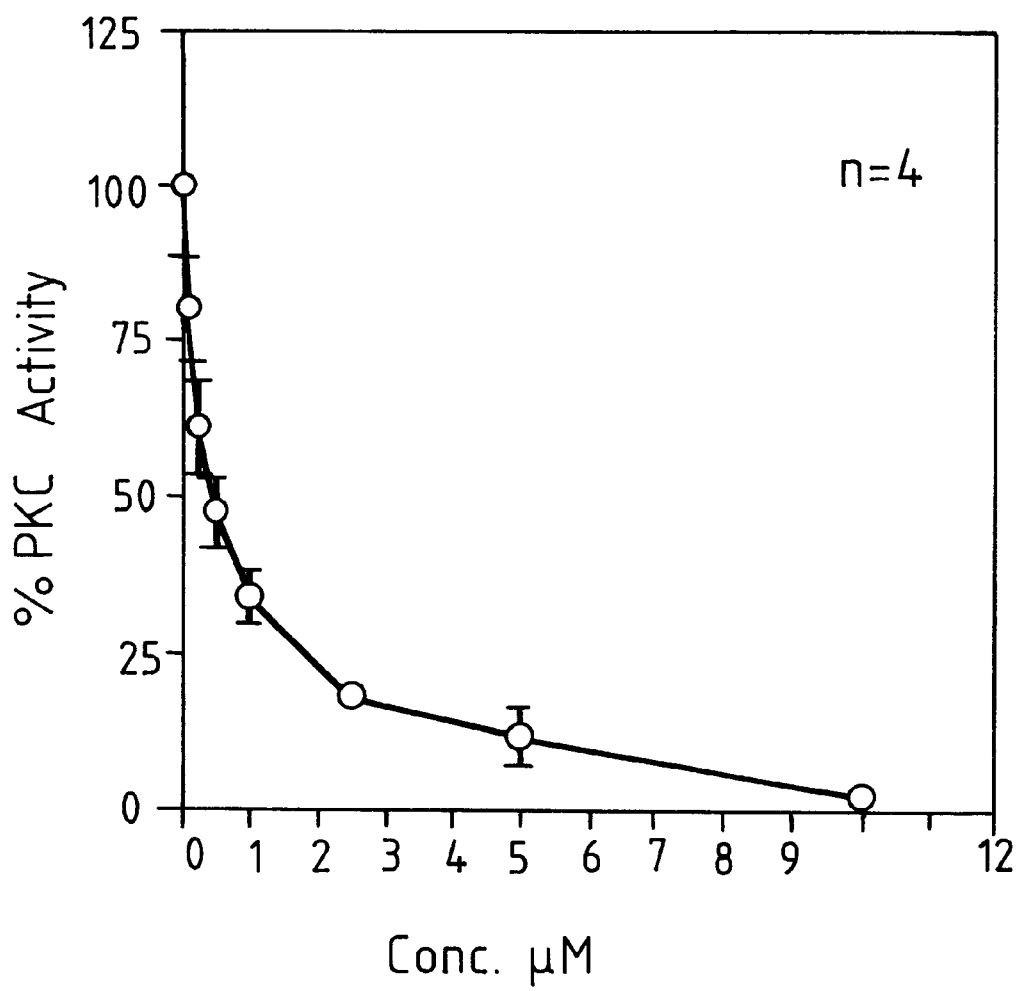
FIG. 2. Effect of gravin fragment (SEQ ID NO:3) on PKC activity toward the peptide substrate VRKRTLRRL (SEQ ID NO:24).

The AKAP79 31–52 PKC binding site peptide KASMLCFKRRKKAAKLAKPKAG (SEQ ID NO: 23) blocked PKC binding to gravin. This result demonstrates that both gravin and AKAP79 likely bind to a similar site on PKC. Further similarity to AKAP79 was demonstrated when the gravin 265–556 (SEQ ID NO: 3) fragment was shown to inhibit PKC activity toward peptide substrate VRKRTLRRL (SEQ ID NO: 24) (Sigma Chemical Co., St. Louis, Mo.) with an $IC_{50}$ of 0.50±0.12 μM (n=4) (FIG. 2). In contrast, the RII binding peptide did not inhibit the kinase. PKC activity was assayed as described [Orr et al., *J. Biol. Chem.*, 269:27715–27718, 1994] in a reaction containing 40 mM HEPES (pH 7.5), 10 mM $MgCl_2$, 0.3 mM $CaCl_2$, 1 mM DTT, 100 μM [$\lambda^{32}P$] adenosine triphosphate (ATP) (500 cpm/pmol), phosphatidylserine (20 μg/ml), and epidermal growth factor receptor peptide (VRKRTLRRL) (SEQ ID NO: 24) as substrate at 30° C. for 10 min. PKC βII (20 ng/μl) was diluted 1:10 in 20 mM Tris (pH 7.9), 1 mg/ml bovine serum albumin (BSA) and 1 mM DTT. Inhibition constants ($IC_{50}$) were determined over an inhibition concentration range of 0.1 to 10 μM gravin 265–556 fragment (SEQ ID NO: 3).

To date, three classes of PKC-binding proteins have been identified by gel overlay and two-hybrid techniques [Faux et al., *Cell*, 70:8–12 (1996a)]. PKC substrate/binding proteins [Chapline et al., 1993] and Receptors for Activated C-kinase (RACKs) [Mochly-Rosen et al., *Proc. Natl. Acad. Sci. USA*, 88:3997–4000, (1991)] have been detected by the gel-overlay procedure, while Proteins that Interact with C-kinase (PICKS), have been isolated in two-hybrid screens [Staudinger et al., 1995]. The data provided herein shows that a region of approximately 290 amino acids supports PKC-binding and fragments corresponding to that region block kinase activity in vitro.

EXAMPLE 5

Monoclonal antibodies are prepared by immunizing Balb/c mice subcutaneously with gravin or gravin fragments in complete Freund's adjuvant (CFA). Subsequent immunizations in CFA or incomplete Freund's adjuvant is performed to increase immune response.

The spleen of the immunized animal is removed aseptically and a single-cell suspension is formed by grinding the spleen between the frosted ends of two glass microscope slides submerged in serum free RPMI 1640, supplemented with 2 mM L-glutamine, 1 mM sodium pyruvate, 100 units/ml penicillin, and 100 μg/ml streptomycin (RPMI) (Gibco, Canada). The cell suspension is filtered through sterile 70-mesh Nitex cell strainer (Becton Dickinson, Parsippany, N.J.), and washed twice by centrifuging at 200 g for 5 minutes and resuspending the pellet in 20 ml serum free RPMI. Thymocytes taken from naive Balb/c mice are prepared in the same manner.

$2 \times 10^8$ spleen cells are combined with $4 \times 10^7$ NS-1 cells (kept in log phase in RPMI with 11% fetal bovine serum (FBS) for three days prior to fusion), centrifuged and the supernatant is aspirated. The cell pellet is dislodged and 2 ml of 37° C. PEG 1500 (50% in 75 mM HEPES, pH 8.0) (Boehringer Mannheim) is added while stirring over the course of one minute, followed by the addition of 14 ml of serum free RPMI over seven minutes. Additional RPMI can be added and the cells are centrifuged at 200 g for 10 minutes. After discarding the supernatant, the pellet is resuspended in 200 ml RPMI containing 15% FBS, 100 mM sodium hypoxanthine, 0.4 mM aminopterin, 16 mM thymidine (HAT) (Gibco), 25 units/ml IL-6 (Boehringer Mannheim) and $1.5 \times 10^6$ thymocytes/ml. The suspension is dispensed into ten 96-well flat bottom tissue culture plates (Corning, United Kingdom) at 200 μl/well. Cells are fed on days 2, 4, and 6 days post-fusion by aspirating 100 μl from each well with an 18 G needle (Becton Dickinson), and adding 100 μl/well plating medium containing 10 U/ml IL-6 and lacking thymocytes.

When cell growth reaches 60–80% confluence (day 8–10), culture supernatants are taken from each well and screened for reactivity to gravin by ELISA. ELISAs are performed as follows. Immulon 4 plates (Dynatech, Cambridge, Mass.) were coated at 4° C. with 50 μl/well with 100 ng/well of p1110δ:GST or GST in 50 mM carbonate buffer, pH 9.6. Plates are washed with PBS with 0.05%, Tween 20 (PBST) and blocked 30 minutes at 37° C. with 0.5% Fish Skin Gelatin. Plates are washed as described above and 50 μl culture supernatant is added. After incubation at 37° C. for 30 minutes, 50 μl of horseradish peroxidase conjugated goat anti-mouse IgG(fc) (Jackson ImmunoResearch, West Grove, Pa.) [diluted 1:10,000 in PBST] is added. Plates are incubated at 37° C. for 30 minutes, washed with PBST and 100 μl of substrate, consisting of 1 mg/ml TMB (Sigma) and 0.15 ml/ml 30% $H_2O_2$ in 100 mM Citrate, pH 4.5, is added. The color reaction is stopped with the addition of 50 ml of 15% $H_2SO_4$. $A_{450}$ is read on a plate reader (Dynatech).

Polyclonal antibodies are prepared by immunizing an animal with an antigen comprising a polypeptide of the present invention and collecting antisera from the immunized animal. A variety of animal species including rabbit, chicken, mouse, rat, or guinea pig are useful in preparation of polyclonal antibodies. The 1130–1780 (SEQ ID NO: 17) gravin fragment was used to prepare polyclonal antibodies in rabbit. Rabbit polyclonal antisera R3698 was produced from the 1130–1780 gravin fragment (SEQ ID NO: 17) by a commercial laboratory (Bethyl Labs, Montgomery, Tex.). The 1130–1780 fragment (SEQ ID NO: 17) was made by preparing and expressing a polynucleotide encoding the 1130–1780 fragment (SEQ ID NO: 9) (generated by PCR using the 5' primer, CCGCCATGGTGCATATGTCCGAGTCCAGTGAGC, (SEQ ID NO: 9) and the 3' primer, GGAGGATCCAGAGATTCTGTAGTTCTG (SEQ ID NO: 13)) as described in Example 2. In addition, the 265–556 fragment (SEQ ID NO: 3) was used to prepare polyclonal antibodies in rabbit and chicken. Rabbit polyclonal antisera, R4310 and chicken polyclonal antisera were produced from the 265–556 fragment (SEQ ID NO: 3) by Bethyl Labs.

Two additional polyclonal antisera were prepared. Two rabbits (4037J and 3548J) were immunized (R&R Rabbitry, Stanwood, Wash.) with 25–50 µg of recombinant gravin fragment 265–556 for a total of three injections and a final boost. Test sera and pre-immune sera were tested by Western blot analysis. Recombinant protein (1 µg/lane) and lysates from HEL cells (25 µg/lane) grown with or without 40 µg/ml PMA to induce gravin expression were separated by 4–12% SDS-PAGE (Novex, San Diego, Calif.) and transferred to immobilon by standard techniques. Resulting blots were incubated in blocking buffer (TBS with 5% milk proteins) to partially renature immobilized protein, then probed with rabbit sera (1:500 dilution in blocking buffer). Unbound antibodies were removed by washing in TBS, followed by incubation with a secondary goat anti-rabbit horse radish peroxidase (HRP) conjugated antibody (1:7500 dilution) in blocking buffer. Unbound antibody was washed away and the blots were developed by enhanced chemiluminescence (ECL, Dupont-NEN, Boston, Mass.) and exposed on film.

Sera from both rabbits recognized the recombinant gravin fragment. A 250 kDa band was detected in the PMA stimulated HEL cell lysate, but not in the lysate prepared from unstimulated REL cells. Serum from rabbit 4037J had the higher sensitivity by Western blot and so this antibody was purified by Protein A affinity chromatography.

EXAMPLE 6

Phorbol ester treatment of a human erythroleukemia cell line (HEL) (HEL 92.1.7, ATCC TIB 180) induces morphological, functional and biochemical changes that are characteristic of macrophage-like cells. One hallmark of this process is the robust induction of gravin [Gordon et al., 1992]. Therefore, the PKA and PKC binding protein profile of HEL cells after prolonged exposure to phorbol esters was examined.

HEL cells were grown in RPMI 1640 containing 12% fetal calf serum and 4 mM glutamine. Gravin expression was induced by culturing with 40 nM phorbol myristate acetate (PMA) for 18 hr. Cell lysates were prepared from either adherent cells grown in the presence of PMA, rinsed with PBS and scraped from the interior of 150 $cm^2$ flasks or from suspension cultures of HEL cells grown in the absence of PMA. Cell pellets were washed twice with PBS prior to resuspension in 20 mM TrisHCl, pH 7.4, 150 mM NaCl, 10 mM EDTA, 0.25% Triton X-100, 0.05% Tween 20, 0.02% $NaN_3$, 10 mM benzamidine, 2 µg/ml pepstatin, 2 µg/ml leupeptin, 4 mM 4-(2-aminoethyl)-benzenesulfonyl fluoride hydrochloride (Lysis Buffer) and incubation on ice for 10 min. The extracts were then centrifuged for 10 min at 16,000×g at 4° C. and the cell lysate supernatant was collected. Protein concentrations were measured using the Bio-Rad DC Protein Assay kit.

The extracts from control and treated cells were subjected to western blot analysis with an affinity purified antibody raised against residues 130 to 1780 of gravin (See Example 5). PMA treatment caused an induction of a 250 kDa protein that specifically reacted with anti-gravin antibodies. Subsequent overlay assays demonstrated that PMA treatment induced the expression of a 250 kDa PKC-binding protein and an RII-binding protein of the same size.

Concomitant with the macrophage-like shift, HEL cells undergoing PMA treatment become adherent and display a considerable cytoplasmic spread [Papayannopoulou et al., Blood, 62:832–845 (1983)]. This sometimes results in the formation of actin stress fibers and causes a general flattening of the cell. In order to establish whether gravin aligned with the actin cytoskeleton, phorbol ester treated HEL cells were stained with rhodamine phalloidin as a marker for actin as described below.

HEL cells were grown on glass coverslips in the presence of 40 nM PMA for 18 hr, rinsed with PBS, fixed in 3.7% formaldehyde and extracted in −20° C. absolute acetone. Cells were rehydrated for 1 hr in PBS and 0.2% BSA and then incubated with either affinity purified anti-gravin antibody, R3698, at 0.5 µg/ml or pre-immune IgG at 0.5 µg/ml. After 1 hr the coverslips were carefully washed in PBS and 0.2% BSA and incubated with either a mixture of FITC conjugated donkey anti-rabbit secondary antibody (1:100 dilution, Jackson ImmunoReasearch Laboratories Inc, West Grove, Pa.) and rhodamine conjugated phalloidin (1 unit/coverslip, Molecular Probes, Inc, Eugene, Oreg.) or secondary antibody alone. In situ RII-overlays were performed essentially as described [Coghlan et al., J. Biol. Chem., 269:7658–7665 (1994)]. Prior to incubation with primary antibody, cells were incubated with 80 nM recombinant murine RII for 2 hr and unbound RII removed by washing three times in PBS and 0.2% BSA. The immobilized RIIα was detected immunochemically with affinity purified goat anti-murine RII (1 µg/ml) and Texas red conjugated donkey anti-goat IgG secondary (1:100 dilution, Jackson ImmunoReasearch Laboratories Inc, West Grove, Pa.). Control coverslips were treated with the antibody to RII in the absence of exogenous murine RII. Cells were examined using a Leica confocal laser scanning system equipped with a Leitz Fluovert-FU inverted microscope and an argon/krypton laser.

All of the cells displayed a concentration of actin to the periphery. In contrast, gravin staining was predominantly cytoplasmic and only a subset of the cells (approximately 25%) expressed large quantities of the protein. Variable levels of gravin expression were not unexpected as HEL cells represent a heterogeneous population at different stages of differentiation [Papayannopoulou et al., 1983]. Superimposition of images of cells stained for actin and cells stained for gravin showed that both proteins exhibit distinct but partially overlapping subcellular distributions. Control experiments were negative when cells were stained with preimmune serum. More detailed confocal analysis of HEL cells detected gravin staining toward the periphery of the cell and enriched in filopodia at the adherent surface. These findings indicate that gravin functions to enhance HEL cell adhesion to the substratum.

Co-localization of Gravin and PKA

In vitro binding studies described in Examples 2 and 4 indicate that gravin is a kinase scaffold protein. Therefore, co-localization experiments were initiated to determine whether a gravin signaling complex could be detected in HEL cells. Fixed and permeabilized cells pre-treated with PMA were overlayed with recombinant murine RIIα. RII-binding in situ was detected with antibodies that specifically recognize murine RII and mimicked the staining pattern for gravin. Since control experiments confirmed that the anti-murine RII antibodies did not detect the endogenous human RII, the increased RII staining was due to direct association with gravin. This conclusion was supported by additional control experiments showing that in situ RII-binding was blocked by incubation with the Ht 31 anchoring inhibitor peptide.

Finally, the gravin signaling complex was isolated by two complementary biochemical methods: immunoprecipitation and affinity chromatography on cAMP-agarose.

Immunoprecipitation of gravin was performed as follows. HEL cell lysates (200 μl of 15 mg/ml) prepared as described above were incubated with either 15 μg of affinity purified anti-gravin or 15 μg of pre-immune IgG at 4° C. for 18 hr. Immune complexes were isolated by the addition of 200 μl of 10% (v/v) Protein A-Sepharose CL-4B (Sigma, St Louis, Mo.) which had been pre-equilibrated in Lysis Buffer. Following incubation at 4° C. for 90 min the beads were washed once in 0.5 M NaCl Lysis Buffer and four times in excess 20 mM TrisHCl, pH 7.4, 150 mM NaCl. The PKA catalytic subunit was released from the immune complex by incubating the Protein-A beads in 200 μl 1 mM cAMP, 20 mM TrisHCl, pH 7.4, 150 nM NaCl for 15 min. The eluate was TCA precipitated prior to analysis on a 4–15% SDS-PAGE gel, electroblotted onto nitrocellulose and the catalytic subunit was detected, as previously described. For the immunoprecipitation and detection of gravin, elution was accomplished by boiling the washed beads in SDS-PAGE sample buffer, separation of proteins on a 4–15% denaturing PAGE gel (5 μg/lane), transfer to nitrocellulose and analysis by gravin western, PKC overlay and RII overlay western [as described above and previously [Klauck et al., 1996].

Gravin was affinity purified by incubating HEL cell lysates (400 μl of 15 mg/ml, prepared as described above with the addition of 10 mM IBMX to the buffer), with 200 μl packed cAMP-agarose (Sigma, St Louis, Mo.) which had been equilibrated in Lysis Buffer with 10 mM IBMX. The slurry was gently mixed for 18 hr at 4° C. and then washed with 1.5 ml Lysis Buffer with 1 M NaCl followed by four 1.5 ml washes with 20 mM TrisHCl, pH 7.4, 150 mM NaCl. Elution was accomplished by incubating the beads in 0.5 ml 75 mM cAMP, 20 mM TrisHCl, pH 7.4, 150 mM NaCl for 30 min at room temperature. The final wash and the eluate were TCA precipitated and the entire sample loaded into a single lane on a 4–15% SDS-PAGE gel. The separated proteins were blotted to nitrocellulose and gravin was identified by western analysis as described above.

Immunoprecipitation with gravin antibodies specifically isolated a 250 kDa protein that could be faintly detected when SDS gels were stained with Coomassie Blue. This 250 kDa protein was present only in immunoprecipitates using the affinity purified gravin antibodies and was not detected in control experiments performed with pre-immune serum. Western blot and overlay assays confinred that the 250 kDa protein was gravin. Moreover, co-precipitation of the PKA holoenzyme was demonstrated by detection of the catalytic subunit in fractions eluted from the immunoprecipitate with cAMP but not in experimental fractions treated with pre-immune serum. The R subunit in the immunoprecipitates was undetectable because the 54 kDa protein migrates with the same mobility as the IgG heavy chain. However, the R subunit/gravin complex was purified from PMA induced HEL cell extracts by affinity chromatography on cAMP-agarose. After extensive washing in high salt buffers, gravin was eluted from the affinity resin with 75 mM cAMP. Since free gravin is refractive to the affinity resin, the protein detected in the eluate was associated with the regulatory subunit. Both co-purification techniques strongly suggest that the PKA holoenzyme is associated with gravin in vivo.

EXAMPLE 7

As previously discussed, thus far gravin has only been detected in human fibroblasts, neurons and endothelial cells. To determine if gravin has a more broad cell distribution or could be induced in other cell types, antibody 4037J was used against lysates of primary human cells and a variety of human, monkey, rat and murine cell lines to detect expression by Western blot analysis.

Preparation of Cells

Primary peripheral blood mononuclear cells (PBMC) were isolated from heparinzied peripheral blood from adult volunteers. Blood was diluted 1:1 with CMF-PBS and centrifuged over Histopaque (Sigma, St. Louis, Mo.) at a density of 1.096 g/cm$^{-3}$ for thirty minutes at 400×g. The resulting interface was collected and washed in CMF-PBS. Monocytes were isolated from PBMC (prepared as above) by an one hour incubation in a 100 mmn polystyrene culture plate (Corning) in RPMI media supplemented with 10% fetal bovine serum. Non-adherent cells were washed away with CMF-PBS. Adherent cells (monocytes) were scraped from the plastic with a rubber spatula, then washed in PBS. Polymorphonuclear cells (PMN) were islated from peripheral blood using the red blood cell/granulocyte fraction of the histopaque procedure described above. The cell pellet was resuspended in an equal volume of CMF-PBS and 3% dextran (Pharmacia, Uppsala, Sweden) in 0.9% NaCl for thirty minutes to allow for sedimentation of the red blood cells. The PMN enriched supernatant was collected and washed three times in CMF-PBS. Between washes residual red blood cells were subjected to hypotonic lysis in 1 ml of water for thirty seconds. Remaining cells were returned to isotonic conditions with 50 ml of CMF-PBS.

The following human cell lines were obtained from ATCC (American Type Culture Collection, Rockville, Md.) and maintained in RPMI±10% fetal bovine serum: HEL (human erythroleukemia), A549 (human lung epithelia), HEK 293 (human embryonic kidney), HL60 (human promyelocytic leukemia), KU812 (immature human basophilic leukocyte), Jurkat (human T cell lymphoma), THP1.1 (human moncyte), RBL2H3 (rat basophilic leukemia), COS (monkey fibroblast), RAW309 (murine monocyte), RAW264.7 (murine monocyte), 3T3L1 (murine embryonic fibroblast), L929 (murine fibroblast) and EL4IL-2 (murine thymoma).

The cell cultures were incubated overnight in the presence of 40 ng/ml PMA, 10 ng/ml lipopolysaccharide (LPS), $10^{-8}$M f-met-leu-phe (fMLP) (all from Sigma, St. Louis, Mo.) or 10 ng/ml tumor necrosis factor alpha (TNFα, Boehringer Mannheim, Indianapolis, Ind.) to determine if gravin expression could be stimulated. Lysates from cell pellets were prepared and protein concentrations determined as previously described in Example 6. Cell lysates were assayed for gravin by western blot as described usin, Protein-A purified anti-gravin antibody 4037J at 5 μg/ml.

Expression of Gravin in Various Cell Lines

Western analysis showed that a 250 Kd band was detected in several human cell lines including KU812, REK293, A549, THP 1.1 and murine cell lines 3T3L1 and L929. For primary human cells, only adherent monocytes expressed the 250 kDa band. With the exception of PMA stimulation of HEL cells (see Example 6), this band was not induced in any other cells with either PMA, LPS, fMLP or TNFα. These bands were confirmed to be RII binding proteins by an overlay assay as described in Example 2. The cells that expressed gravin shared a common feature of adherence to plastic or growth in cell clusters.

Co-immunoprecipitation of Gravin and RII

HEK293 cells were harvested from culture and a lysate was prepared as described in Example 4. HEK293 lysate (100 μg) was incubated with 10 μg of either 4037J (anti-gravin polyclonal) or 241A (anti-human RII monoclonal) antibody for two hours on ice. An equal volume of pre-washed Protein G-Sepharose beads (Pharmacia, Uppsala, Sweden) were added and samples incubated for one hour on a rotor at 4° C. The beads were washed three times in lysis buffer, then once in PBS. SDS sample buffer was added to the beads which were then boiled for two minutes at 100° C. The samples were spun down and the supernatant recovered. The samples were run on to a 4–12% SDS-PAGE gel in duplicate lanes along with antibody (2 μg), and cell lysate (25 μg) as controls. Proteins were transferred to immobilon by standard techniques. Western analysis was performed on the resulting blots by the methods described in 6. One blot was probed with 4037J antibody and detected with a goat anti-rabbit IgG-HRP and the other blot was incubated with 241A antibody and detected with goat anti-mouse IgG-HRP.

In the gravin Western a 250 kDa band was detected in lanes containing the cell lysate, 4037J co-immunoprecipiate. and the 241A co-imunoprecipitate samples. In the RII western a 54 kDa band was detected in the cell lysate. In the lanes containing the 4037J and 241A co-immunoprecipitates, a doublet was detected with one band at 54 kDa and another band running slightly higher. This upper band aligned with the IgG lane indicating the lower band to be RII. These results demonstrate that gravin and RII are associated in cells and can be co-immunoprecipitated from cell lysates using either an anti-gravin or an anti-RII antibody.

EXAMPLE 8

The nicotinic acetylcholine receptor is a neurotransmitter-gated ion channel comprising five transmembrane polypeptides. The five polypeptides appear to form a transmembrane aqueous pore through which cations can flow. In response to the binding of acetylcholine, the ion channel "opens" and permits the flow of Na$^+$ into the cell (sodium current). The influx of sodium ions causes membrane depolarization which signals the muscle to contract. Individual receptors appear to rapidly open and close during the period of time that acetylcholine remains bound to the receptor. Within a few hundred milliseconds of acetylcholine binding, the channel closes and prevents further flow of sodium current and the acetylcholine signal is terminated.

The sensitivity of the nicotinic acetylcholine receptor to acetylcholine is attenuated by the phosphorylation of the transmembrane polypeptides (desensitization). Prolonged exposure of the receptor to acetylcholine leads to desensitization of the receptor. PKA appears be involved in desensitization of the nicotinic acetylcholine receptor by phosphorylating serine and tyrosine residues of the five transmembrane polypeptides. *Myasthenia gravis* is an autoiminune disease associated with the development of antibodies to the nicotinic acetylcholine receptors.

The present invention contemplates that gravin functions to localize PKA and PKC to a particular subcellular area of the cell. The role of gravin in coordination of PKA and PKC targeting to cytoskeletal components would be analogous to the role of AKAP79 role in clustering PKA, PKC, and protein phosphatase 2B at the postsynaptic density which is a specialized structure of the dendritic cytoskeleton [Coghlan et al., 1995b; Klauck et al., 1996; Rosenmund et al., *Nature*, 368:853–856 (1994)1.

Modulators which inhibit or abolish binding between gravin and PKA and/or PKC are useful in modulating the localization of PKA and/or PKC to particular subcellular regions. These modulators may include polypeptides which specifically bind to gravin or fragments of gravin which bind to PKA and/or PKC, and other non-peptide compounds (e.g. isolated or synthetic organic or inorganic molecules) which specifically interact with gravin or fragments of gravin.

EXAMPLE 9

An assay to determine the binding of gravin to binding partners was developed. The C-terminal clone, HF9, containing the RII binding region of gravin, was cloned into a Thioredoxin (Trx) bacterial expression vector as described below. The C-terminal clone, pBSII9 (described in Example 3), containing the RII binding region of gravin in was cloned into a Thioredoxin (Trx) bacterial expression vector. Briefly, to construct a thioredoxin expression vector, an XbaI/HindIII thioredoxin fragment was subclonsed into pUC 19 containing a lac Z gene and a tacZ promotoer. The resulting plasmid was designated TRX F/S pUC19. In order to insert the HF9 clone into TRX F/S pUC19, an NcoI site was created with an oligonucleotide: Met1153, 5= TACAA CCATGGACAGGCTATCCCC. (The NCO cleavage site is underlined). The 3' oligonucleotide used was T7 (Strategene). Amplification of pBS/HF9 with the two oligo-nucleotides resulted in a 3 kb fragment which was digested with NcoI and XhoI (the latter provided the polylinker of pBS). Then NcoI/XhoI fragment was ligated in frame with the thioredoxin gene in TRX F/S pUC19 (predigested with NcoI/XhoI). The fusion protein was expressed in *E. Coli*, induced with 1 mM IPTG to O.D.$_{600}$ of 0.7 at 30° C. Cells were harvested, lysed with French Press under standard conditions.], The protein-protein binding assays were performed as follows. Briefly, anti-Trx mouse monoclonal antibodies were passively captured onto Immulon plates (Dynatech) in PBS. Anti-Trx monoclonal antibody was prepared using the methods described in Example 5. Nonspecific sites in the wells were blocked at room temperature for one hour with a buffer containing 2.5% milk in 50 mM sodium citrate and 145 mM sodium chloride. E coli lysate containing Trx/C-terminal gravin was added to wells in PBS/0.2% BSA for overnight at 4° C. Free and non-specific proteins were removed with several washes with PBS. Biotinylated RII (chemically biotinylated using standard procedures) was then used as a ligand, and added in PBS/0.02% BSA. After three hours of incubation at room temperature, unbound proteins were removed with multiple washes of PBS/0.05% Tween 20. Streptavidin-Eu (Wallac) was diluted 1:1000 in assay buffer (Wallac) and added to detect biotinylated RII/gravin complexes. After additional washes in PBS/0 05% Tween to remove non-specifically bound proteins, Enhancement solution (Wallac) diluted 1:1 in water was added and release of europium was measured by increased fluorescence using a DELFIA$^R$ Research Fluormeter (Model 1232, Wallac).

This protein-protein binding assay indicated that over 50% of the binding to gravin was pecific. Biotinylated RII bound to gravin in a specific and saturable manner. The Kd for the interaction was found to be approximately 50 nM, similar to that reported in Nauert el al, 1996 using surface plasmon resonance.

EXAMPLE 10

The amino acid sequence of gravin exhibits some similarity to SSeCKS/clone 322/clone 72 [Chapline et al., 1996]. There is approximately 69% homology in the first 1,000 amino acids of gravin and SSeCKS. Gravin also exhibits some homology in selected regions to myristoylated alanine rich PKC substrate (MARCKS) [Aderein, Cell, 71:713–716 (1992)]. However, the remainder of each of the protein sequences are distinct. Also, gravin is a protein of 1780 amino acids which migrates with a mobility of 250 kDa on SDS gels, whereas SSeCKS/clone 72 is 1687 residues and migrates at 207 kDa [Lin et al., (1995), Chaplin, et al., (1995) and National Center for Biotechnology Information accession no. 2210332A]. In addition, the identification of five prospective nuclear localization signals has led to the idea that SSeCKS is a nuclear protein [Lin et al., 1995], whereas immunochemical data clearly shows that gravin is cytoplasmic and likely to be a cytoskeletal component. Clone 322 was described as being a tumor suppressor gene which is down regulated in oncogene transformed cells. Based upon a sequence similarities between gravin and clone 72 (and clone 322), gravin may also function as a tumor suppressor gene.

It is well known in the art that cancerous cells are non-adhesive cells. The non-adhesive nature of malignant cancer cells allows these cells to metastasize. The release or de-adhesion of a cancer cell from matrix proteins or other cells is prerequisite to migration or metastasis to new sites. Transformed or tumorigenic cells may be converted to a less tumorigenic state by increased expression of cytoplasmic proteins such as alpha actinin or talin that function in cytoskeletal reorganization, adhesion and migration [Gluck et al., Cell Science, 107:1773–1782 (1994)].

A tissue survey has shown that gravin exhibits a restricted cellular distribution and is predominantly expressed in fibroblasts, neurons and cells derived from the neural crest [Grove et al., 1994]. Since each of these cell types participates in adherent, migratory or path-seeking functions, it was postulated that gravin may regulate membrane/cytoskeleton events [Grove et al., 1994]. This view has been further substantiated by the immunolocalization experiments described in Example 6 which indicates that gravin may concentrate PKA in the ruffles and filopodia of adherent HEL cells. In addition, the data disclosed in Example 6 point toward a role for gravin in cell adhesion. Phorbol ester induced adhesion in HEL cells [Papayannopoulou et al., 1983] is concomitant with the increased gravin expression; whereas loss of an adherent phenotype upon transformation of REF 52 fibroblasts with an SV40 derivative is coincident with the down-regulation of clone 72 [Chapline et al., 1996]. Since phosphorylation events help to maintain the integrity of the membrane/cytoskeleton it is also tempting to speculate that PKA and PKC anchoring by gravin may play a role in adherent processes.

Given that gravin is expressed in adherent cells, but not in non-adherent cells, and given that clone 72 is down-regulated in oncogene transformed cells, gravin is implicated in cancer biology. Similar to its function in localizing kinases near the nicotinic acetylcholine receptor, gravin may also localize one or more kinases near a cell adhesion molecule wherein the response to cellular signals or other stimuli causes the phosphorylation of the cell adhesion molecule. It has been reported that substitution of threonine residues in the cytoplasmic domain of the LFA-1β subunit abolishes LFA-1 mediated cell adhesion [Hibbs, et al., J.Exp. Med., 174:1227–1238 (1991)]. These threonine residues appear to be phosphorylated during cellular activation [Valmu et al., J. Immunol., 155:1175–1183 (1995)]. These residues are conserved in other integrin β subunits. Thus, phosphorylation may regulate cell adhesion mediated by several distinct integrins.

Modulators which inhibit or abolish binding between gravin and its binding partner are useful in modulating localization of the binding partner by gravin. For example, modulators may interfere with the localization of a kinase near cell adhesion molecules. These modulators may include polypeptides which specifically bind to gravin or fragments of gravin which bind to a gravin binding partner, and other non-peptide compounds (e.g. isolated or synthetic organic or inorganic molecules) which specifically interact with gravin or fragments of gravin.

Numerous modifications and variations in the practice of this invention are expected to occur to those of skill in the art. Consequently, only such limitations as appear in the appended claims should be placed on the invention.

What is claimed:

1. A purified and isolated polynucleotide encoding a cAMP-dependent protein kinase (PKA)-binding polypeptide fragment of gravin (SEQ ID NO: 5).

2. The polynucleotide of claim 1 wherein the polypeptide fragment of gravin does not bind protein kinase C (PKC).

3. The polynucleotide of claim 2 encoding amino acid residues 1130–1780 of SEQ ID NO: 5.

4. The polynucleotide of claim 2 encoding amino acid residues 1130–1582 of SEQ ID NO: 5.

5. The polynucleotide of claim 2 encoding amino acid residues 1526–1780 of SEQ ID NO: 5.

6. The polynucleotide of claim 2 encoding amino acids residues 1526–1582 of SEQ ID NO: 5.

7. The polynucleotide of claim 2 encoding amino acid residues 1537–1563 of SEQ ID NO: 5.

8. A purified and isolated polynucleotide encoding a protein kinase C (PKC)-binding polypeptide fragment of gravin (SEQ ID NO: 5).

9. The polynucleotide of clam 8 wherein the polypeptide fragment of gravin does not bind cAMP dependent protein kinase (PKA).

10. The polynucleotide of claim 9 encoding amino acid residues 265–556 of SEQ ID NO: 5.

11. The polynucleotide of claim 9 encoding amino acid residues 295–316 of SEQ ID NO: 5.

12. The polynucleotide of claim 9 encoding amino acid residues 514–536 of SEQ ID NO: 5.

* * * * *

UNITED STATES PATENT AND TRADEMARK OFFICE
CERTIFICATE OF CORRECTION

PATENT NO. : 6,090,929
DATED : July 18, 2000
INVENTOR(S) : John D. Scott et al.

It is certified that error appears in the above-identified patent and that said Letters Patent is hereby corrected as shown below:

Column 59, line 50, please delete "1130-1780" and insert --1129-1780--.

Column 59, line 58, please delete "1537-1563" and insert --1526-1563--.

Column 60, line 46, please delete "clam 8" and insert --claim 8--.

Signed and Sealed this

Tenth Day of April, 2001

Attest:

NICHOLAS P. GODICI

Attesting Officer     *Acting Director of the United States Patent and Trademark Office*